US008574879B2

(12) United States Patent
Gaddy et al.

(10) Patent No.: US 8,574,879 B2
(45) Date of Patent: *Nov. 5, 2013

(54) METHODS FOR INCREASING THE PRODUCTION OF ETHANOL FROM MICROBIAL FERMENTATION

(75) Inventors: James L. Gaddy, Fayetteville, AR (US); Dinesh K. Arora, Fayetteville, AR (US); Ching-Whan Ko, Fayetteville, AR (US); John Randall Phillips, Fayetteville, AR (US); Rahul Basu, Bethlehem, PA (US); Carl V. Wilkstrom, Benton, AR (US); Edgar C. Clausen, Fayetteville, AR (US)

(73) Assignee: Ineos Bio Limited, Lisle, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/325,149

(22) Filed: Dec. 14, 2011

(65) Prior Publication Data
US 2012/0094346 A1  Apr. 19, 2012

Related U.S. Application Data

(63) Continuation of application No. 11/876,312, filed on Oct. 22, 2007, which is a continuation of application No. 10/311,655, filed as application No. PCT/US01/23149 on Jul. 23, 2001, now Pat. No. 7,285,402.

(60) Provisional application No. 60/220,794, filed on Jul. 25, 2000.

(51) Int. Cl.
C12P 7/06  (2006.01)

(52) U.S. Cl.
USPC ........ 435/161; 435/140; 435/162; 435/262.5; 435/266

(58) Field of Classification Search
None
See application file for complete search history.

(56) References Cited

U.S. PATENT DOCUMENTS

| | | | |
|---|---|---|---|
| 4,351,905 | A | 9/1982 | Clyde |
| 4,393,136 | A | 7/1983 | Cheetham |
| 4,400,470 | A | 8/1983 | Zeikus |
| 4,654,123 | A | 3/1987 | Berg |
| 4,737,459 | A | 4/1988 | Zeikus |
| 4,886,751 | A | 12/1989 | Thorsson |
| 5,173,429 | A | 12/1992 | Gaddy |
| 5,182,199 | A | 1/1993 | Hartley |
| 5,593,886 | A | 1/1997 | Gaddy |
| 5,807,722 | A | 9/1998 | Gaddy |
| 5,821,111 | A | 10/1998 | Grady |
| 6,136,577 | A | 10/2000 | Gaddy |
| 6,340,581 | B1 | 1/2002 | Gaddy |
| 6,919,488 | B2 | 7/2005 | Melnichuk |
| 7,285,402 | B2 | 10/2007 | Gaddy |

FOREIGN PATENT DOCUMENTS

| | | |
|---|---|---|
| WO | WO 98/00558 | 1/1998 |
| WO | WO 00/68407 | 11/2000 |

OTHER PUBLICATIONS

Abrini, J., Naveau, H., & Nyns, E.J. (1994). *Clostridium autoethanogenum*, Sp-Nov, An Anaerobic Bacterium That Produces Ethanol from Carbon-Monoxide. *Archives of Microbiology*, 161(4), 345-351.
Bailey, J.E., & Ollis, D.F. (1986). *Biochemical Engineering Fundamentals* (2$^{nd}$ ed.): McGraw-Hill Brook Company.
Bioloen, P., Helle, N.J., & Sachtler, W.M.H. (1979). Incorporation of surface carbon into hydrocarbons during Fischer-Tropsch synthesis: Mechanistic Implication, *Journal of Catalysis*, 58(1), 95-107.
Brady, R.C. & Pettit, R. (1981). On the mechanism of the Fiascher-Tropsch reaction: The chain propagation step. *Journal of American Chemical Society*, 103, 1287-1289.
Bredwell, M.D., Srivastava, P., Warden, R.M. (1999). Reactor Design Issues for Synthesis-Gas Fermentations. *Biotechnol. Prog.* 15, 834-844.
Byung Hong Kim, P.B., Datta, R. & Zeikus, J.G. (1984). Control of Carbon and Electron Flow in *Clostridium acetobutylicum* Fermentations: Utilization of Carbon monoxide to Inhibit Hydrogen Production and to enhance butanol yields. *Applied Environmental Microbilgy*, 48(4), 764-770.
Chang, I.S., Kim, B.H., Kim, D.H., Lovitt, R.W., & Sung, H.C. (1999). Formulation of defined media for carbon monoxide fermentation by *Eubacterium limosum* KIST612 and the growth characteristics of the bacterium. *Journal of Bioscience and Bioengineering*, 88(6), 682-685.
Chang, I.S., Kim, D.H., Kim, B.H., Shin, P.K., Sung, H.C., & Lovitt, R.W. (1998). CO fermentation of *Eubacterium limosum* KIST612. *Journal of Microbiology and Biotechnology*, 8(2), 134-140.
Diekert, G. & Wohlfarth, G. (1994). Metabolism of Homoacetogens. *Antonie Van Leeuwenhoek International Journal of General and Molecular Microbiology*, 66(1-3), 2009-221.
Dry, M.E. (2002). The Fischer-Tropsch process: 1950-20000, *Catalysis Today*, 71(3-4), 227-241.
Fischer, F. & Tropsch, H. (1926). Synthesis of petroelum from gasification products of coal at normal pressure, *Berichte der Deutschen Chemischen Gesellschaft [Abteilung] B: Abhandlungen*, 59B, 830-1, 8326.
Girbal, L., Croux, C., Vasconcelos, I., & Soucaille, P. (1995). Regulation of metabolic shifts in *Clostridium acetobutylicum* ATCC 824. *FEMS Microbiology Reviews*, 17(3), 287-297.

(Continued)

Primary Examiner — Irene Marx
(74) Attorney, Agent, or Firm — Vikrant B. Panchal; Ineos Bio Limited

(57) ABSTRACT

A stable continuous method for producing ethanol from the anaerobic bacterial fermentation of a gaseous substrate containing at least one reducing gas involves culturing in a fermentation bioreactor anaerobic, acetogenic bacteria in a liquid nutrient medium; supplying the gaseous substrate to the bioreactor; and manipulating the bacteria in the bioreactor by reducing the redox potential, or increasing the NAD(P)H TO NAD(P) ratio, in the fermentation broth after the bacteria achieves a steady state and stable cell concentration in the bioreactor. The free acetic acid concentration in the bioreactor is maintained at less than 5 g/L free acid. This method allows ethanol to be produced in the fermentation broth in the bioreactor at a productivity of greater than 10 g/L per day. Both ethanol and acetate are produced in a ratio of ethanol to acetate ranging from 1:1 to 20:1.

13 Claims, 2 Drawing Sheets

(56) References Cited

OTHER PUBLICATIONS

Girlbal, L., Vasconcelos, I., Saint-Amans, S., & Soucaille, P. (1995). How neutral red modified carbon and electron flow in *Clostridium acetobutylicum* grown in chemostat culture at neutral pH. *FEMS Microbiology Reviews*, 16(23), 151-162.

Gottschal, J.C., & Morris, J.G. (1981). The Induction of Acetone and Butanol Production in Cultures of *Clostridium-acetobutylicum* by Elevated Concentrations of Acetate and Butyrate. *FEMS Microbiology Letters*, 12(4), 385-389.

Hansen, J.B. (1997). High conversion of synthesis gas into oxygenates. Studies in Surface Science and Catalysis, 61, 457-67.

Harwood, C.S., & Gibson, J. (1988). Anaerobic and aerobic metabolism of diverse aromatic compounds by the photosynthetic bacterium *Rhodopseudomonas palustris* Applied and Environmental Microbiology, 54, 712-717.

Hyman M.R. & Artp, D.J. (1991). Kinetic analysis of the interaction of nitric oxide with the membrane-associated, nickel and iron-sulfur-containing hydrogenase from *Azotobacter vinelandii*. *Biochimica et Biophysica Acta*, 1076, 165-172.

Jung, G.Y., Jung, H.O., Kim, J.R., Ahn, Y., & Park, S. (1999). Isolation and characterization *Rhodopseudomonas palustris* P4 which utilizes CO with the production of $H_2$. *Biotechnology Letters*, 21(6), 525-529.

Kashket, E.R., :& Zhi-Yi Cao. (1995). Clostridial strain degeneration. *FEMS Microbiology Reviews*, 17(3), 307-315.

Klasson, K.T., Ackerson, M.D., Clausen, E.C., & Gaddy, J.L. (1992) Bioconversion of synthesis gas into liquid or gaseous fuels. *Enzyme and Microbial Technology*, 14(8), 602-608.

Klasson, K.T., Ackerson, M.D., Clausen, E.C., & Gaddy, J.L. (1993). Biological Conversion of Coal and Coal-Derived Synthesis Gas. *Fuel*, 72(12), 1673-1678.

Klasson, K.T., Lundback, K.M.O., Clausen, E.C., :& Gaddy, J.L. (1993). Kinetics of Light Limited Growth and Biological Hydrogen-Production from Carbon-Monoxide and Water by *Rhodospirillum-rubrum*. *Journal of Biotechnology*, 29(1-2), 177-188.

Klier, K. (1982). Methanol synthesis. *Advances in Catalysis*, 31, 243-313.

Krasna, A.I. (1979). Hydrogenase: Properties and applications. *Enzyme and Microbial Technology*, 1(3), 165-172.

Krasna, A.I., & Rittenberg, D. (1954). The inhibition of hydrogenase by nitric oxide. *Proceedings of the National Academy of Sciences*, 40(4), 225-227.

Kutzenok, A., & Aschner, M. (1952). Degenerative Processes in a Strain of *Clostridium butylicum*. *Journal of Bacteriology*, 64(6), 829-836.

Lemon, B.J., & Peters, J.W. (1999). Binding of exogenously added carbon monoxide at the active site of the iron-only hydrogenase (CpI) from *Clostridium pasteurianum*. *Biochemistry*, 38(40), 12969-12973.

Ljungdahl, L.G. (1986), The autotrophic pathway of acetate synthesis in acetogenic bacteria. *Annual Review of Microbiology*, 40, 415-450.

Meyer, C.L., Mclaughlin, J.K., & Papoutsakis, E.T. (1985). The Effect of CO on Growth and Product Formation in Batch Cultures of *Clostridium acetobutylicum*. *Biotechnology Letters*, 7(1), 37-42.

Meyer, C.L., & Papoutsakes, E.T. (1989). Increased Levels of ATP and NADH are Associated with increased Solvent Production in Continuous Cultures of *Clostridium acetobutylicum*. *Applied Microbiology and Biotechnology*, 30(5), 450-459.

Meyer, C.L., Roos, J.W., & Papoutsakes, E.T. (1986). Carbon-Monoxide Gasing Leads to Alcohol Production and Butyrate Uptake without Acetone Formation in Continuous Cultures of *Clostridium acetobutylicum*. *Applied Microbiology and Biotechnology*, 24(2), 159-167.

Misoph, M., & Drake, H.L. (1996). Effect of $CO_2$ on the fermentation capacities of the acetogen *Peptostreptococcus productus* U-1. *Journal of Bacteriology*, 178(11), 3140-3145.

Pichler, H., & Schulz, H. (1970). Recent results in the synthesis of hydrocarbons from carbon monoxide and hydrogen. *Chemie Ingenieur Technik*, 42(18), 1162-74.

Ragsdale, S. (1991). Enzymology of the Acetyl-CoA Pathway of $CO_2$ Fixation. *Critical Reviews in Biochemistry and Molecular Biology*, 26, 261-300.

Rao, G., & Mutharasan, R. (1989). NADH Levels and Solventogenesis in *Clostridium-acetobutylicum*—New Insights through Culture Fluorescence. *Applied Microbiology and Biotechnology*, 30(1), 59-66.

Sarup, B. & Wojciechowski, B.W. (1989). Studies of the Fischer-Tropsch synthesis on a cobalt catalyst. II. Kinetics of carbon monoxide conversion to methane and to higher hydrocarbons. *Canadian Journal of Chemical Engineering*, 67(1), 62-74.

Schlegel, H.G., & Bowien, B. (1989). *Autotrophic bacteria*. Madison, WI, Berlin; New York: Science Tech Publishers, Springer-Verlag.

Seefeldt, L.C., & Arp, D.J. (1989). Oxygen Effects on the Nickel-Containing and Iron-Containing Hydrogenase from *Azotobacter vinelandii*. *Biochemistry*, 28(4), 1588-1596.

Steynberg, A.P., Espinoza, R.L., Jager, B., & Vosloo, A.C. (1999). High-temperature Fischer-Tropsch synthesis in commercial practice. *Applied Catalysis, A: General*, 186(1,2), 41-54.

Tibelius, K.H., & Knowles, R. (1984). Hydrogenase activity in *Azospirillum brasilense* is inhibited by nitrite, nitric oxide, carbon monoxide and acetylene. *Journal of Bacteriology*, 160(1), 103-106.

Vasconcelos, I., Girbal, L., & Soucaille, P. (1994). Regulation of Carbon and Electron Flow in *Clostridium acetobutylicum* Grown in Chemostat Culture at Neutral Ph on Mixtures of Glucose and Glycerol. *Journal of Bacteriology*, 176(5), 1443-1450.

Vega, J.L., Clausen, E.C., & Gaddy, J.L. (1990). Design of bioreactors for coal synthesis gas fermentations. *Resources, Conservation and Recycling*, 3(2-3), 149-160.

Vega, J.L., Prieto, S., Elmore, B.B., Clausen, E.G., & Gaddy, J.L. (1989). The Biological Production of Ethanol from Synthesis Gas. *Applied Biochemistry and Biotechnology*, 20-1, 781-797.

Wood, H.G., Ragsdale, S.W., & Pezacka, E. (1986a). The Acetyl-CoA pathway—a Newly Discovered Pathway of Autotrophic Growth. *Trends in Biochemical Sciences*, 11(1), 14-18.

Wood, H.G., Ragsdale, S..W., & Pezacka, E. (1986b). The Acetyl-CoA Pathway of Autotrophic Growth. *FEMS Microbiology Reviews*, 39(4), 345-362.

Wood, H.G., Ragsdale, S.W., & Pezacka, E. (1986c). A New Pathway of Autotrophic Growth Utilizing Carbon-Monoxide or Carbon-Dioxide and Hydrogen. *Biochemistry International*, 12(3), 421-440.

Worden, R.M., Bredwell, M.D., & Grethlein, A.J. (1997). Engineering issues in synthesis-gas fermentation, *Furels and Chemicals from Biomass*, 666,321-335.

Zennaro, R., Bartholomew, C.H. and Tagliabue, M. (2000). Kinetics of Fischer-Tropsch synthesis on Titania-supported Cobalt. *Catalysis Today*., 58(4), 309-319.

Thorsson, "Process for Producing Ethanol by Fermenting Molasses," English abstract of Hungarian Patent No. HU 201971-B.

Liou et al., "*Clostridium carboxidivorans* sp. nov., a Solvent-Producing *Clostridium* Isolated from an Agricultural Settling Lagoon, and Reclassification of the Acetogen *Clostridium scatologenes* strain SL1 as *Clostridium drakei* sp. nov.," Int. J. Sys. Evol. Microbiol., 55:2085-2091 (Sep. 2005).

Klasson et al., "Biological Production of Liquid and Gaseous Fuels from Synthesis Gas" Appl. Biochem. Biotechnol., Proceedings of the 11th Symposium on Biotechnology for Fuels and Chemicals, 24/25:857 (1990).

Phillips et al., "Biological Production of Ethanol from Coal Synthesis Gas-Medium Development Studies" Appl. Biochem. Biotechnol., Proceedings from the 14th Symposium on Biotechnology for Fuels and Chemicals, 39/40:559 (1993).

Rothstein et al., "*Clostridium thermosaccharolyticum* Strain Deficient in Acetate Production," J. Bacteriol, 165(1):319-320 (Jan. 1986).

Lovitt et al., "Ethanol Production by Thermophilic Bacteria: Biochemical Basis for Ethanol and Hydrogen Tolerance in *Clostridum thermohydrosulfuricum*," J. Bacteriol., 170(6):2809 (Jun. 1988).

Taherzadeh et al., "The Effects of Pantothenate Deficiency and Acetate Addition on Anaerobic Batch Fermentation of Glucose by *Saccharomyces cerevisiae*," Appl. Microbiol. Biotechnol., 46:176-182 (Sep. 1996).

(56) References Cited

OTHER PUBLICATIONS

Bahl et al., "Continuous Production of Acetone and Butanol by *Clostridium acetobutylicum* in a Two-Stage Phosphate Limited Chemostat," Eur. J. Appln. Microbiol. Biotechnol 15(4):201-205 (Oct. 1982).

Bahl et al., "Nutritional Factors Affecting the Ratio of Solvents Produced by *Clostridium acetobutylicum*," Appl. Environ. Microbiol., 52(1):169-172 (Jul. 1986).

Reardon et al., "Metabolic Pathway Rates and Culture Fluorescence in Batch Fermentations of *Clostridium acetobutylicum*," Biotechnol. Prog., 3(3):153-168 (Sep. 1987).

Terracciano et al., "Intracellular Conditions Required for Initiation of Solvent Production by *Clostridium acetobutylicum*," Appl. and Environ. Microbiol., 52(1):86-91 (Jul. 1986).

Long et al., "Sporulation of *Clostridium acetobutylicum* P262 in a Defined Medium," Appl. Environ. Microbiol., 45(4):1389-1393 (Apr. 1983).

Ferras et al., "Acetonobutylic Fermentation: Improvement of Performances by Coupling Continuous Fermentation and Ultrafiltration," Biotechnol. Bioengin.,28:523 (Apr. 1986).

Clarke et al., "Nature and Significance of Oscillatory Behaviour during Solvent Production by *Clostridium acetobutylicum* in Continuous Culture," Biotechnol. Bioengin., 32:538-544 (Aug. 1988).

Martin et al., "Effects of Acetic and Butyric Acids on Solvent Production by *Clostridium acetobutylicum*," Biotechnol. Lett., 5(20):89-94 (Feb. 1983).

Bryant et al., "Buffering as a Means for Increasing Growth and Butanol Production by *Clostridium acetobutylicum*," J. Indust. Microbiol., 3:49:55 (Feb. 1988).

Husemann et al., "Solventogenesis in *Clostridium acetobutylicum* Fermentations related to Carboxylic Acid and Proton Concentrations," Biotechnol. Bioengin., 32:843-852 (Sep. 1988).

Barik et al., "Biological Production of Alcohols from Coal through Indirect Liquefaction," Appl. Biochem. Biotechnol., Proceedings of the $9^{th}$ Symposium on Biotechnol. for Fuels and Chemicals, 18:363 (1988).

Vega et al., "The Biological Production of Ethanol from Synthesis Gas," Appl. Biochem. Biotechnol., Proceedings of the $10^{th}$ Symposium on Biotechnol. for Fuels and Chemicals, 20/21:781 (1989).

Landuyt et al., Transition from Acid Fermentation to Solvent Fermentatiaon in a Continuous Dilution Culture of *Clostridium thermosaccharolyticum*, Annals of New York Academy of Sciences, pp. 473-478 (Dec. 1987).

Lynd et al., "Thermophilic Ethanol Production," Appl. Biochem. Biotechnol., 28/29: 549 (1991).

Degraef et al., "The Steady-State Internal Redox State (NADH/NAD) Reflects the External Redox State and is Correlated with Catabolic Adaptation in *Escherichia coli*," J. Bacteriol., 181(8): 2351-2357 (Apr. 1999).

Hols et al., "Acetate Utilization in *Lactococcus lactis* Deficient in Dehydrogenase: A Rescue Pathway for Maintaining Redox Balance," J. Bacteriol., 181(17):5521 (Sep. 1999).

Rao et al., "Altered Electron Flow in a Reducing Environment in *Clostridium acetobutylicum*," Biotechnol. Lett., 10(2):129-132 (Feb. 1988).

Kim et al., "Redox Potential in Acetone-Butanol Fermentations," $9^{th}$ Symposium on Biotechnology for Fuels and Chemicals, Boulder, CO (May 5-8, 1987).

Kim et al., "Electron Flow Shift in *Clostridium acetobutylicum* Fermentation by Electrochemically Introduced Reducing Equivalent," Biotechnol. Lett., 10(2):123-128 (Feb. 1988).

Phillips et al., "Synthesis Gas as Substrate for the Biological Production of Fuels and Chemicals," Appl. Biochem. and Biotechnol., Proceedings of the $15^{th}$ Symposium on Biotechnology for Fuels and Chemicals, 45/46:145 (1994).

Rao et al., "Directed Metabolic Flow with High Butanol Yield and Selectivity in Continuous Culture of *Clostridium acetobutylicum*," Biotechnol. Lett., 10(5):313-318 (May 1988).

Rao et al., "Manipulation of End-Product Distribution in Strict Anaerobes," Annals of New York Academy of Science, pp. 76-83 (Nov. 1987).

Murray et al., "Ethanol Production by a Newly Isolated Anaerobe, *Clostridium saccharolyticum*: Effects of Culture Medium and Growth Conditions," Canad. J. Microbiol., 29:342 (Mar. 1983).

Ram et al., "Ethanol Production by *Clostridium thermocellum* SS8, A Newly Isolated Thermophilic Bacterium," Biotechnol. Lett., 11(8):589-592 (Aug.1989).

Ingram et al., "Expression of Different Levels of Ethanologenic Enzymes from *Zymomonas mobilis* in Recombinant Strains of *Escherichia coli*," Appl. Environ. Microbiol., 54(2):397-404 (Feb. 1988).

Guedon et al., Carbon and Electron Flow in *Clostridium cellulolyticum* Grown in Chemostat on Synthetic Medium, J. Bacteriol., 181(10):3262-3269 (May 1999).

Grahame et al., "Substrate and Cofactor Reactivity of a Carbon Monoxide Dehydrogenase-Corrinoid Enzyme Complex: Stepwise Reduction of Iron-Sulfur and Corrinoid Centers, the Corrindoid Co2+/1+ Redox Midpoint Potential, and Overall Synthesis of Acetyl-CoA," Biochem., 32:10786-10793 (Oct. 12, 1993).

Gottwald et al., "The Internal pH of *Clostridium acetobutylicum* and its Effect on the Shift from Acid to Solvent Formation," Arch. Microbiol., 143:42-46 (Oct. 1985).

Examination Report dated Dec. 8, 2003, issued in counterpart European Patent Application No. 01954884.1.

Examiner's Report dated Jul. 29, 2005, issued in counterpart Malaysian Patent Application No. PI20013724.

METHODS FOR INCREASING THE PRODUCTION OF ETHANOL FROM MICROBIAL FERMENTATION

CROSS REFERENCE TO RELATED APPLICATIONS

This application is a divisional of U.S. patent application Ser. No. 10/311,655, filed Mar. 11, 2003, now U.S. Pat. No. 7,285,402 which is a US national phase of International Patent Application No. PCT/US01/23149, filed Jul. 23, 2001, which claims the benefit of the priority of U.S. Provisional Patent Application No. 60/220,794, filed Jul. 25, 2000, now abandoned. Other applications include: U.S. Ser. Nos. 11/876,312, 13/313,136, 13/316,963, 13/314,862, 13/323, 913, 13,330442, 13/331,156, 13/331,182, 13/331192.

BACKGROUND

The present invention is directed to improvements in microbial fermentation methods for the production of ethanol from a gaseous substrate containing at least one reducing gas using anaerobic (or facultative) acetogenic bacteria.

Methods for producing ethanol, among other organic acids, alcohols, hydrogen and organic acid salts, from the microbial fermentation of gaseous substrates in media containing suitable nutrients and trace minerals using certain anaerobic bacteria have been disclosed by these inventors. For example, the inventors have previously disclosed that dilute gas mixtures are introduced into a bioreactor containing one or more strains of anaerobic bacteria that utilize the waste gas components by a direct pathway to produce a desired compound. The compound is recovered from the aqueous phase in a separate vessel or vessels, utilizing a suitable recovery method for the compound produced. Examples of recovery methods include extraction, distillation or combinations thereof, or other efficient recovery methods. The bacteria can be removed from the aqueous phase and recycled to the bioreactor to maintain high cell concentrations, thus maximizing productivity. Cell separation, if desired, is accomplished by centrifugation, membranous filtration, or other techniques. See, for example, International Patent Publication No. WO98/00558, published Jan. 8, 1998; U.S. Pat. No. 5,807,722; U.S. Pat. No. 5,593,886 and U.S. Pat. No. 5,821,111.

In addition to its major product, acetic acid, strains of the anaerobic bacterium *Clostridium ljungdahlii* are able to also produce ethanol as a product in the conversion of carbon monoxide (CO), hydrogen ($H_2$) and carbon dioxide ($CO_2$). The production of acetic acid ($CH_3COOH$) and ethanol ($C_2H_5OH$) from CO, $CO_2$ and $H_2$ are shown by the following overall stoichiometric equations:

(1)

(2)

(3)

(4)

Several exemplary strains of *C. ljungdahlii* include strain PETC (U.S. Pat. No. 5,173,429); strain ERI-2 (U.S. Pat. No. 5,593,886) and strains C-01 and O-52 (U.S. Pat. No. 6,136, 577). These strains are each deposited in the American Type Culture Collection, 10801 University Boulevard, Manassas, Va. 20110-2209, under Accession Nos.: 55383 (formerly ATCC No. 49587), 55380, 55988, and 55989 respectively.

Each of the strains of *C. ljungdahlii* is an anaerobic, gram-positive bacterium with a guanine and cytosine (G+C) nucleotide content of about 22 mole %. These bacteria use a variety of substrates for growth, but not methanol or lactate. These strains differ in their CO tolerance, specific gas uptake rates and specific productivities. In the "wild" strains found in nature, very little ethanol production is noted. Strains of *C. ljungdahlii* operate ideally at 37° C., and typically produce an ethanol to acetyl (i.e. which refers to both free or molecular acetic acid and acetate salts) product ratio of about 1:20 (1 part ethanol per 20 parts acetyl) in the "wild" state. Ethanol concentrations are typically only 1-2 g/L. While this ability to produce ethanol is of interest, because of low ethanol productivity the "wild" bacteria cannot be used to economically produce ethanol on a commercial basis with minor nutrient manipulation the above-mentioned *C. ljungdahlii* strains have been used to produce ethanol and acetyl with a product ratio of 1:1 (equal parts ethanol and acetyl), but the ethanol concentration is less than 10 g/L, a level that results in low productivity, below 10 g/L·day. In addition culture stability is an issue, primarily due to the relatively high (8-10 g/L) concentration of acetyl (2.5-3 g/L molecular acetic acid) in combination with the presence of ethanol. Furthermore, as the gas rate is increased in an effort to produce more ethanol, the culture is inhibited, first by molecular acetic acid and then by CO. As a result, the culture becomes unstable and fails to uptake gas and produce additional product. Further, early work by the inventors showed difficulty in producing more than a 2:1 ratio of ethanol to acetyl in a steady state operation. See, e.g., Klasson et al., 1990 *Applied Biochemistry and Biotechnology*, Proceedings of the 11$^{th}$ Symposium on Biotechnology for Fuels and Chemicals, 24/25: 857; Phillips et al., 1993 *Applied Biochemistry and Biotechnology*, Proceedings of the 14$^{th}$ Symposium on Biotechnology for Fuels and Chemicals, 39/40: 559, among others.

A large number of documents describe the use of anaerobic bacteria, other than *C. ljungdahlii*, in the fermentation of sugars that do not consume CO, $CO_2$ and $H_2$ to produce solvents. In an attempt to provide high yields of ethanol, a variety of parameters have been altered which include: nutrient types, microorganism, specific addition of reducing agents, pH variations, and the addition of exogenous gases. See, e.g., Rothstein et al, 1986 *J. Bacteriol.*, 165 (1):319-320; Lovitt et al, 1988 *J. Bacteriol.*, 170 (6):2809; Taherzadeh et al, 1996 *Appl. Microbial. Biotechnol.*, 46:176.

There remains a need in the art of the handling of industrial gaseous substrates, the ability to extract valuable commodities from such gases, particularly waste gases, such as $H_2$, CO and $CO_2$. There is a need to enhance the production of ethanol relative to the production of the other products normally generated by the fermentation of such gases by acetogenic bacteria.

SUMMARY

In response to the need in the art, the present invention provides novel methods which are continuous, steady state methods and which result in ethanol concentrations greater than 10 g/L and acetate concentrations lower than about 8-10 g/L, while continuing to permit culture growth and good culture stability.

In one aspect, the invention provides a stable continuous method for producing ethanol from the anaerobic bacterial fermentation of a gaseous substrate. The method comprising the steps of culturing in a fermentation bioreactor anaerobic, acetogenic bacteria in a liquid nutrient medium and supplying to the bioreactor the gaseous substrate comprising at least one reducing gas selected from the group consisting of CO and $H_2$. The bacteria in the bioreactor are manipulated by reducing the redox potential, or increasing the NAD(P)H TO NAD (P) ratio, in the fermentation broth after the bacteria achieves a steady state, e.g., a stable cell concentration, in the bioreactor. The free acetic acid concentration in the bioreactor is maintained at less than 5 g/L free acid. The culturing and manipulating steps cause the bacteria in the bioreactor to produce ethanol in a fermentation broth at a productivity greater than 10 g/L per day. Both ethanol and acetate are produced in the fermentation broth in a ratio of ethanol to acetate ranging from to 20:1.

In one embodiment of this method, the manipulating step includes one or more of the following steps: altering at least one parameter selected from the group consisting of nutrient medium contents, nutrient feed rate, aqueous feed rate, operating pressure, operating pH, gaseous substrate contents, gas feed rate, fermentation broth agitation rate, product inhibition step, cell density, and substrate inhibition.

In another embodiment of this method, the manipulating step comprises supplying to the bioreactor said gaseous substrate comprising the reducing gas, CO, at a desired rate of uptake. This rate is desirably from 0.3 to 2 mmol CO/gram of dry cell of bacteria in said bioreactor/minute.

In still another embodiment of this method the manipulating step comprises feeding into said fermentation bioreactor said nutrient medium comprising a limiting amount of calcium pantothenate. The calcium pantothenate is desirably in a range of from 0.5 to 50 µg/grams of dry cell of bacteria produced in the bioreactor.

Another embodiment of the method includes supplying excess $H_2$ reducing gas to said bioreactor prior to providing the limiting amount of calcium pantothenate.

In yet a further aspect, the invention provides a method in which the manipulating step of the method includes feeding into said fermentation bioreactor said nutrient medium comprising a limiting amount of cobalt. Desirably, the amount of cobalt is in a range of from 5 to 100 µg cobalt/grams of dry cell of bacteria produced in said bioreactor.

In another embodiment, the method of the invention includes preventing acclimation of said bacteria in said bioreactor to said amount of cobalt by maintaining a constant cobalt concentration and adjusting one or more parameters, such as gas rate, liquid rate, agitation rate and $H_2$ gas partial pressure.

Additional optional steps of these methods include subjecting a sample of the broth to centrifugation to eliminate cells and to gas chromatography to monitor the maintenance of the ratio and/or productivity values.

In another embodiment, the method comprises feeding as the gaseous substrate an amount of $H_2$ in slight excess of the stoichiometric amount for ethanol production. In still another embodiment, the gaseous substrate further comprises an amount of CO in slight excess of the amounts required by the bacteria, wherein uptake of $H_2$ by the bacteria is inhibited and the NAD(P)H to NAD(P) ratio in the broth is increased.

In yet another embodiment of the method, a step is provided in which inhibition by molecular acetic acid is reduced by increasing the aqueous feed rate when the molecular acetic acid present in the fermentation broth approaches or exceeds 2 g/L.

In another embodiment of the method, the manipulating step may include agitating the medium, bacteria and gaseous substrate in the bioreactor at a selected agitation rate. For example, reduction in the agitation rate reduces the amount of CO transferred to the fermentation broth. This reduction in the rate of CO transfer causes an increase in $H_2$ conversion, so that the reducing gas, $H_2$, is present in the bioreactor in excess of the growth requirements of the bacteria. The gas rate may also be similarly reduced to decrease the amount of CO transferred, thereby increasing $H_2$ conversion, so that the reducing gas, $H_2$, is present in the fermentation bioreactor in excess of the growth requirements of the bacteria.

In still another embodiment of the method, the bacterial culture may initially be brought to the desired cell concentration in the bioreactor before limiting the calcium pantothenate or cobalt concentration of the nutrient medium.

In another embodiment of the method of this invention, a two stage CSTR (bioreactor) is used which consists of a growth reactor which feeds the fermentation broth to a production reactor in which most of the ethanol is produced.

In another aspect of the invention, the method described above includes the optional steps of: recovering ethanol by removing the fermentation broth from the bioreactor; distilling ethanol from the broth; and recovering the ethanol. Additionally or preferably, a sample of the broth is subjected to centrifugation to eliminate cells; and the maintenance of the ratio is monitored using gas chromatography.

In still another aspect, the method of the invention may further employ an additional step of recycling water (containing up to 5 g/L acetyl) from the ethanol production back to the reactor so that an equilibrium is established between the ethanol and acetyl in the reactor. As a result, more of the CO, $CO_2$ and $H_2$ fed to the reactor and converted to products results in ethanol production.

Other aspects and advantages of the present invention are described further in the following detailed description of the preferred embodiments thereof.

DETAILED DESCRIPTION

Figure 1:
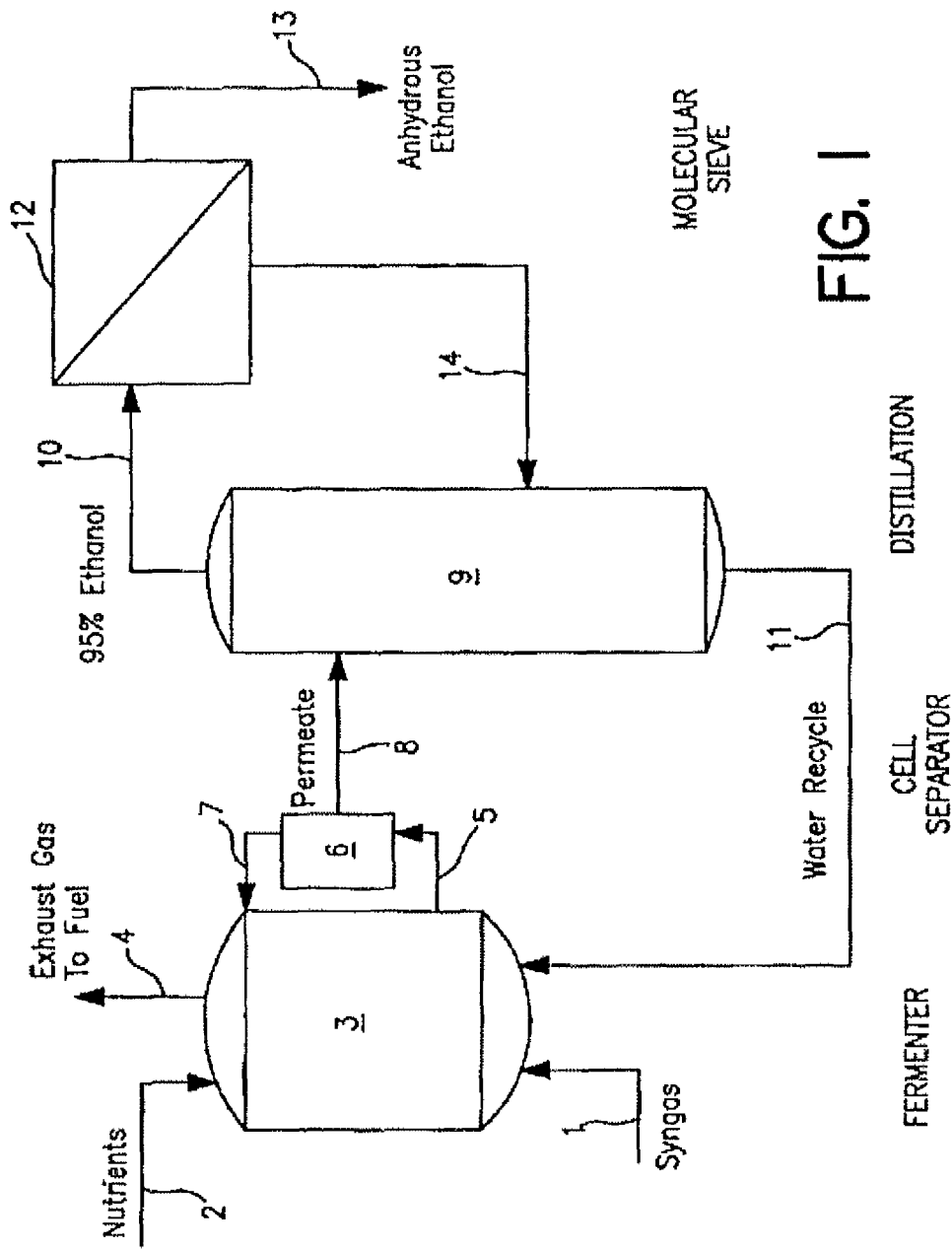
FIG. 1 is a schematic diagram illustrating a continuous fermentation method with product recovery according to this invention. Gaseous substrate 1 and liquid phase nutrient medium 2 are fed to bioreactor 3 containing the subject bacterial culture. Conversion of the gaseous substrate to ethanol and acetic acid takes place in the bioreactor 3. Exhaust gas 4 containing gases other than CO, CO, and $H_2$ and unconverted CO, $CO_2$ and $H_2$ from bioreactor 3 are vented, combusted as fuel or flared. With cell recycle, liquid effluent 5 is sent to cell separator 6 where the cells 7 and cell-free permeate 8 are separated. Cells 7 are sent back to bioreactor 3 and permeate 8 is sent to product recovery. Ethanol can be recovered from the permeate 8 (or alternatively from the effluent 5 if cell separation is not employed). Permeate 8 is separated in distillation column 9 to produce 95% ethanol overhead 10, and water 11 for recycle back to bioreactor 3. The 95% ethanol overhead 10 is sent to a molecular sieve 12 where anhydrous ethanol 13, the desired final product, is separated from dilute ethanol 14 which is sent back to the distillation column 9.

The present invention involves methods for the anaerobic fermentation of gaseous substrates containing at least one reducing gas, particularly the gaseous components of industrial waste and synthesis gases (e.g., CO, $CO_2$ and $H_2$) to ethanol. These methods yield ethanol productivities greater than 10 g/L·day by manipulating the biological pathways of the subject bacteria. One method of the invention causes an abundance of NAD(P)H over NAD(P). The oxidation of NAD(P)H to NAD(P) causes acetic acid produced by the culture to be reduced to ethanol. Alternatively, other methods for the production of high concentrations of ethanol in an anaerobic fermentation of this invention involve reducing the redox potential of the fermentation broth, and thereby reducing acetic acid to ethanol. The methods of this invention produce high ethanol concentrations (i.e., greater than about 10 g/L, and preferably greater than about 15 g/L) and low acetate concentrations (i.e. less than about 5 g/L free acetic acid in the bioreactor). These methods also maintain and control method conditions for continuous ethanol and acetic acid production to help the system recover rapidly from method upsets. Further, the methods of this invention help prevent culture acclimation to low nutrient concentration, which can be detrimental to culture performance. The present invention provides a viable commercial method for ethanol production.

I. Definitions

Unless otherwise defined, the following terms as used throughout this specification are defined as follows.

The term "continuous method" as used herein refers to a fermentation method which includes continuous nutrient feed, substrate feed, cell production in the bioreactor, cell removal (or purge) from the bioreactor, and product removal. This continuous feeds, removals or cell production may occur in the same or in different streams. A continuous process results in the achievement of a steady state within the bioreactor. By "steady state" is meant that all of these measurable variables (i.e., feed rates, substrate and nutrient concentrations maintained in the bioreactor, cell concentration in the bioreactor and cell removal from the bioreactor, product removal from the bioreactor, as well as conditional variables such as temperatures and pressures) are constant over time.

The term "gaseous substrates" as used herein means CO alone, CO and $H_2$, $CO_2$ and $H_2$, or CO, $CO_2$ and $H_2$, optionally mixed with other elements or compounds, including nitrogen and methane in a gaseous state. Such gaseous substrates include gases or streams, which are typically released or exhausted to the atmosphere either directly or through combustion. In some embodiments of this method the gaseous substrate comprises CO. In other embodiments of this method, the gaseous substrate comprises $CO_2$ and $H_2$. In still other embodiments, the gaseous substrate comprises CO and $H_2$. In a particularly preferred embodiment, the gaseous substrate comprises CO, $CO_2$ and $H_2$. Still other substrates of the invention may include those components mentioned above and at least one gas of nitrogen, $CO_2$, ethane and methane. Thus, such substrates include what is conventionally referred to as "syngas" or synthesis gas from the gasification of carbon products (including methane), as well as waste gases from a variety of industrial methods.

The term "reducing gas" means either or both CO or $H_2$. By the phrase "an amount of reducing gas greater than that required for growth of the bacteria" means that amount of reducing gas that exceeds the amount that the bacteria can use for growth or metabolism, given the nutrient medium ingredients. This amount can be achieved by increasing the net amount of reducing gas, or by reducing key nutrient ingredients, so that the excess amount of gas is achieved without increasing the gas, or by increasing the rate of gas delivery to the bacteria. When the bacteria are exposed to more reducing gas than required for growth, the bacteria respond by increasing the producing of ethanol.

"Subject bacteria" are acetogenic anaerobic (or facultative) bacteria, which are able to convert CO and water or $H_2$ and $CO_2$ into ethanol and acetic acid products. Useful bacteria according to this invention include, without limitation, *Acetogenium kivui*, *Acetobacterium woodii*, *Acetoanaerobium noterae*, *Clostridium aceticum*, *Butyribacterium methylotrophicum*, *C. acetobutylicum*, *C. thermoaceticum*, *Eubacterium limosum*, *C. ljungdahlii* PETC, *C. ljungdahlii* ERI-2, *C. ljungdahlii* C-01, *C. ljungdahlii* O-52, and *Peptostreptococcus productus*. Other acetogenic anaerobic bacteria are selected for use in these methods by one of skill in the art.

By the term "mixed strains," it is meant a mixed culture of two or more of the subject bacteria. Such "mixed strains" of the bacteria enumerated hereinabove are utilized in the methods of this invention.

The terms "bioreactor," "reactor," or "fermentation bioreactor," include a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas lift Fermenter, Static Mixer, or other device suitable for gas-liquid contact. Preferably for the method of this invention, the fermentation bioreactor comprises a growth reactor which feeds the fermentation broth to a second fermentation bioreactor, in which most of the product, ethanol, is produced.

"Nutrient medium" is used generally to describe conventional bacterial growth media which contain vitamins and minerals sufficient to permit growth of a selected subject bacteria. Sugars are not included in these media. Components of a variety of nutrient media suitable to the use of this invention are known and reported in prior publications, including those of the inventors. See, e.g. the nutrient media formulae described in International Patent Publication No. WO98/00558; U.S. Pat. No. 5,807,722; U.S. Pat. No. 5,593,886, and U.S. Pat. No. 5,821,111, as well as in the publications identified above. According to the present invention, a typical laboratory nutrient medium for acetate production from CO, $CO_2$, and $H_2$ contains 0.9 mg/L calcium pantothenate. However, a typical laboratory nutrient medium for ethanol production from CO, $CO_2$, and $H_2$ contains 0.02 mg/L calcium pantothenate.

The terms "limiting substrate" or "limiting nutrient" define a substance in the nutrient medium or gaseous substrate which, during bacterial culture growth in the bioreactor, is depleted by the culture to a level which no longer supports steady state or stable bacterial growth in the bioreactor. All other substances in the nutrient medium or gas substrate are thus present in excess, and are "non-limiting". The evidence for limitation is that an increase in the rate of addition of the limiting substrate, i.e. in the nutrient feed rate or gas feed rate, to the culture causes a corresponding increase in the rate of gas uptake (mmol/min of gas) due to increase in cell density.

Unless stated otherwise, the term "acetate" is used to describe the mixture of molecular or free acetic acid and acetate salt present in the fermentation broth. The ratio of molecular acetic acid to acetate is dependent upon the pH of the system, i.e., at a constant "acetate" concentration, the lower the pH, the higher the molecular acetic acid concentration relative to acetate salt.

"Cell concentration" in this specification is based on dry weight of bacteria per liter of sample. Cell concentration is measured directly or by calibration to a correlation with optical density.

The term "natural state" describes any compound, element, or pathway having no additional electrons or protons that are normally present. Conversely, the term "reduction state" describes any compound, element, or pathway having an excess of one or more electrons. The "reduction state" is achieved by adding one or more electrons to the "natural state", i.e. by lowering the redox potential of the fermentation broth.

"Ethanol productivity" is the volumetric productivity of ethanol, calculated as the ratio of the steady state ethanol concentration and the liquid retention time (LRT) in continuous systems, or the ratio of the ethanol concentration and the time required to produce that concentration in batch systems. The phrase "high ethanol productivity" describes a volumetric ethanol productivity of greater than 10 g/L·day.

The phrase "high concentration of ethanol" means greater than about 10 g/L, preferably greater than 15 g/L ethanol in fermentation broth or a product ratio of ethanol to acetate of 5:1 or more.

"Excess $H_2$" is available for ethanol production when the ratio of the moles of $H_2$ in the feed gas to the sum of two times the moles of CO converted and three times the moles of $CO_2$ converted is greater than 1.0. If this ratio is less than 1.0, excess $H_2$ is not available and ethanol can only be produced through a different controlling mechanism.

II. The Biological Pathways Utilized in the Method of this Invention

Without wishing to be bound by theory, the inventors theorize that the methods for increasing the anaerobic production of ethanol from the methods described herein are based upon the biological pathways involving the conversion of NAD(P)H to NAD(P) in the basic pathway cycles of the acetogenic pathway for autotrophic growth. The invention involves manipulating those pathways to enable continuous production and maintenance of high concentrations of ethanol with low acetate concentrations under stable operating conditions, thereby providing commercially useful methods for ethanol production from industrial gases.

The essential involvement of NAD(P)H to NAD(P) in the biological pathways is described as follows: The production of ethanol from gaseous components, such as CO, $CO_2$, and $H_2$ occurs in a three step biological method. In the first step, the substrates CO and $H_2$ are oxidized and, in doing so, release NAD(P)H:

NAD(P)→NAD(P)H $CO+H_2+H_2O\rightarrow CO_2+4H^+$

The products of step 1 are then converted to acetic acid, a step that requires NAD(P)H:

NAD(P)H→NAD(P)

$CO+CO_2+6H^+\rightarrow CH_3COOH+H_2O$

Finally, if excess NAD(P)H is available because the reaction of step 1 proceeds at a faster rate than the reaction of step 2, acetic acid is reduced to ethanol.

NAD(P)H→NAD(P)

$CH_3COOH+4H^+\rightarrow C_2H_5OH+H_2O$

Thus, the availability of excess NAD(P)H from substrate oxidation leads to the production of ethanol from acetic acid.

There are two known basic pathway cycles in the acetogenic pathway: (1) the Acetyl-CoA cycle and (2) the THF cycle, in which $CO_2$ is reduced to a methyl group. The sequence for the generation of ethanol and acetic acid therefrom is illustrated in J. R. Phillips et al., 1994 *Applied Biochemistry and Biotechnology*, 45/46:145. The Acetyl-CoA cycle has an inner cycle, referred to herein as the CO cycle. As the CO cycle normally reacts clockwise, ferredoxin is reduced. Ferredoxin can also be reduced by $H_2$ as it is oxidized on the enzyme hydrogenase. As a result, the Acetyl-CoA cycle also reacts clockwise, and ferredoxin is oxidized. If the inner CO cycle and the Acetyl-CoA cycle react at the same rates, ferredoxin is in a redox-state equilibrium. If however, these two cycles do not occur at the same rate, i.e., the CO cycle reacts at a faster rate than the Acetyl-CoA cycle, reduced ferredoxin is built up. Also with excess $H_2$, reduced ferredoxin can also be produced in excess. This excess reduced ferredoxin causes the NAD(P) to be regenerated (reduced) to NAD(P)H, which builds an excess that must be relieved to equilibrium and in doing so, reduces acetic acid to ethanol.

The THF cycle functions for cell growth and is necessary for a continuous culture; therefore it cannot be completely stopped. Reducing the THF cycle rate also serves to cause a higher NAD(P)H to NAD(P) ratio. NAD(P)H is oxidized in two places. By limiting this oxidation, which would keep the total cellular NAD(P)H to NAD(P) ratio in balance, the NAD(P)H is used to reduce acetic acid to ethanol.

A second basic method of causing acetic acid to be reduced to ethanol is by directly lowering the redox potential of the fermentation broth. A reduction state sufficiently lower than the natural state of the culture causes NAD(P)H to be in abundance and promote the reduction of acetic acid to ethanol.

III. The Methods of the Invention

The basic steps of the method include the following: A continuous fermentation method with product recovery is described by reference to FIG. 1 and exemplified in Example 1 below. A continuous flow of gaseous substrate 1 comprising at least one reducing gas, e.g., CO or $H_2$, is supplied at a selected gas feed rate and a continuous flow of liquid phase nutrient medium 2 at a selected nutrient feed rate are supplied to a fermentation bioreactor 3 containing a subject bacteria. In the bioreactor 3, the medium and gaseous substrate are fermented by the bacteria to produce ethanol and acetate acid. Once a stable cell concentration is achieved under steady state conditions, the components of the continuous system are manipulated to reduce the redox potential, or increase the NAD(P)H to NAD(P) ratio, in the fermentation broth, while keeping the free acetic acid concentration in the bioreactor less than 5 g/L. The methods of this invention are designed to permit and maintain production of ethanol and acetate in the fermentation broth such that the ethanol productivity is greater than 10 g/L·day at an ethanol to acetate ratio of between 1:1 and 20:1. In one embodiment, that ratio is greater than 3:1. In another embodiment, that ratio is greater than 5:1. In still another embodiment, that ratio is greater than 10:1. In still another embodiment that ratio is greater than 15:1. The method of this invention is alternatively effective in enhancing stable continuous (steady state) production of high ethanol concentrations (15-35 g/L ethanol) and low acetate concentrations (0-5 g/L acetate), i.e., ethanol to acetate product ratio of 3:1 or more, from CO, $CO_2$, and $H_2$ with good method stability.

Periodically, during the course of the methods of this invention, samples of the broth are removed to determine the ratio by a conventional assay method. For example, the cells are separated from the sample, e.g., by centrifugation and the cell-free sample is then subject to an assay method, such as the preferred method of gas chromatography. However, other conventional assay methods are selected by one of skill in the art. The additional optional steps of the method are added to achieve and/or maintain the ratio. Example 2 demonstrates such an assay method.

Steps used to manipulate the system components and maintain and/or achieve the desired ethanol productivity or the ethanol to acetate ratio include at least one, and desirably, combinations of the following steps: altering nutrient medium contents, nutrient feed rate, aqueous feed rate, operating pressure, operating pH, gaseous substrate contents, gas feed rate, fermentation broth agitation rate, avoiding product inhibition step, decreasing cell density in the bioreactor, or preventing substrate inhibition. Some preferred manipulations include supplying the bioreactor with liquid phase nutrient (pantothenate or cobalt) limitation, a slight excess of CO and $H_2$ in the feed gas, minimizing acetate concentration, avoiding culture acclimation to low liquid phase nutrient concentrations, bringing the culture to a suitable cell concentration at a relatively fast rate, raising the pH of the culture above 4.5, purging bacterial cells from the bioreactor to a cell concentration less than the stable steady state concentration that utilizes all reducing gas or nutrient substrates in the bioreactor and increasing the aqueous feed rate when the free acetic acid portion of the acetate present in the fermentation bioreactor broth exceeds 2 g/L, thereby inhibiting any unwanted increase in the concentration of free acetic acid. All of these steps are described in detail below.

Exhaust gas 4 containing gases other than CO, $CO_2$ and $H_2$ and unconverted CO, $CO_2$ and $H_2$ from the reactor are vented from the reactor and are used for their fuel value. If excess $H_2$ as a controlling mechanism is employed, the $H_2$ partial pressure in the outlet gas and ratio of $H_2$ partial pressure to $CO_2$ partial pressure in the exit gas are used to identify the control of the ethanol to acetate ratio by that step. Cell recycle is used (but is not required) to increase the concentration of cells inside the bioreactor, and thus provide more biocatalyst for CO, $CO_2$ and $H_2$ conversion. With cell recycle, liquid effluent from the reactor 5 is sent to a cell separator 6 where the cells 7 and permeate (cell free liquid) 8 are separated. The cells 7 are sent back to the bioreactor and the permeate 8 is sent to product recovery.

Cell separation is accomplished by using a continuous centrifuge, hollow fiber or spiral wound filtration system, ceramic filter system or other solid/liquid separator. Ethanol can be recovered from the permeate (or alternatively the effluent from the reactor 5 if cell separation is not employed) by a variety of techniques including distillation and adsorption. Permeate 8 is separated in a distillation column to produce 95% ethanol overhead 10, and water 11 for recycle back to the reactor 3. The recycle water 11 contains excess nutrients not used in the fermentation, but any excess vitamins from fermentation or cell lysis are destroyed by thermal distillation. The 95% ethanol overhead 10 is sent to a molecular sieve 12 where anhydrous ethanol 13, the desired final product, is separated from dilute ethanol 14 which is sent back to the distillation column 9.

The continuous combination of growth, death and cell purge maintains a constant cell concentration, such that a continuous method used in producing ethanol (and small amounts of acetic acid) can operate for many months by being fed CO, $CO_2$ and $H_2$ along with nutrients without additional culture supplementation. The methods of this invention maintain and control conditions for continuous ethanol and acetic acid production and prevent or correct rapidly for method upsets. The methods of this invention also help prevent culture acclimation to low nutrient concentration, which can be detrimental to culture performance. In the descriptions below and in the examples, unless otherwise indicated, the pressure used is 1 atmosphere and the temperature used is between 36-41° C. Desirable temperatures and pressures may be determined by one of skill in the art, depending on the microorganism selected for use in the bioreactor.

A variety of manipulations, described specifically below, added to the basic steps of this invention permit the enhanced production of ethanol. Preferably, liquid phase nutrient limitation (pantothenate or cobalt) or the use of excess $H_2$ or CO are the method steps of the invention, described in detail below, used to achieve and maintain the desired ethanol productivity and permit production of stable concentrations and ratios of ethanol to acetate in the fermentation broth. These conditions permit production of stable concentrations of ethanol and acetate in the fermentation broth. In a preferred embodiment, the ethanol to acetate product ratio produced in the fermentation broth is greater than 10:1 and the ethanol concentration is greater than 15 g/L.

A. Calcium Pantothenate Limitation

In one specific embodiment of this invention, the method for manipulating the biological pathways to favor ethanol production and limit acetic acid production involves limiting the amount of calcium pantothenate in the nutrient medium to an amount which is less than required to maintain the bacteria at a stable, steady state concentration that would fully utilize the calcium pantothenate provided. Pantothenate is a component of Acetyl-CoA and therefore, by limiting calcium pantothenate in the nutrient medium, the Acetyl-CoA cycle rate is reduced relative to the CO cycle rate. This causes a build-up of reduced ferredoxin and the reduction of NAD(P) to NAD(P)H, and thereby increases the production of ethanol as the final product.

Pantothenate limitation is observed when the micrograms (µg) of calcium pantothenate fed to the reactor per gram (g) of cells (dry weight) produced in the reactor is in the range of 0.5 to 100. A more desirable pantothenate limitation is in the range of 2 to 75 µg of calcium pantothenate per gram (g) of dry cells produced in the reactor. Still a preferred pantothenate limitation is in the range of 0.5 to 50 µg of calcium pantothenate per gram (g) of cells produced in the reactor. Another embodiment of this limitation is at about 1-25 µg of calcium pantothenate per gram (g) of cells produced in the reactor. Another embodiment of this limitation is at about 10-30 µg of calcium pantothenate per gram (g) of cells produced in the reactor. This amount of the nutrient maintains ethanol production in preference to acetate production. One embodiment of this method is illustrated in Example 4.

In another aspect of this method, the acclimation of the bacteria in the fermentation bioreactor to low limiting calcium pantothenate concentration is avoided by regulating or adjusting the fermentation parameters, so that a constant calcium pantothenate concentration is maintained, while at least one, and sometimes more than one, parameter of gas feed rate, liquid feed rate, agitation rate, or $H_2$ partial pressure is adjusted. Major changes in nutrients are avoided, but a relatively constant nutrient feed concentration is maintained. If the culture is allowed to acclimate to low liquid phase limiting nutrients, poor product ratios of 1.0 g ethanol/g acetate or less occurs in an irreversible method. Thus, reactor shut down and reinoculation is necessary. Preferably, the biological pathway is controlled to favor ethanol production and limit acetic acid production by first supplying excess $H_2$ in the feed gas to the bioreactor, and then limiting calcium pantothenate in the nutrient medium as described above.

In fact, at start-up, the normally limiting liquid phase nutrient calcium pantothenate is kept in excess to avoid acclimation to low nutrient concentrations, a condition that can result in very poor performance and the loss of the culture=s ability to produce achieve high ethanol productivities of more than 10 g/L·day if excess $H_2$ is not employed. An example of such regulation of fermentation parameters for a particular bacterial culture is illustrated in Example 17.

B. Cobalt Limitation

In another embodiment of this invention, the method for manipulating the biological pathways to favor ethanol production and limit acetic acid production involves limiting the amount of cobalt in the nutrient medium to an amount which is less than required to maintain the bacteria at a stable steady state concentration that would fully utilize the cobalt provided. Cobalt limitation is observed when the micrograms (μg) of cobalt fed to the reactor per gram (g) of cells (dry weight) produced in the bioreactor is in the range of 5 to 100. Preferably, a cobalt limitation involves providing between about 20 to 50 μg of cobalt to the reactor per gram of cells produced in the reactor. This amount of cobalt maintains ethanol production in preference to acetate in the process. Example 18 illustrates an embodiment of the method of limiting cobalt to the reactor according to this method.

Limiting cobalt in the fermentation broth may also reduce the Acetyl-CoA cycle rate. Because cobalt is used to transfer a methyl group from the THF cycle to the Acetyl-CoA cycle, limiting the amount of cobalt in the fermentation broth also reduces the THF cycle function by not permitting the transfer. Cobalt limitation reduces the THF cycle rate, which also causes a higher NAD(P)H to NAD(P) ratio, thereby producing ethanol.

The method is further manipulated by preventing acclimation to low limiting cobalt concentration. In much the same manner as acclimation to low pantothenate concentrations is avoided, a constant cobalt concentration is maintained while adjusting one or more of the fermentation parameters (gas rate, liquid rate, agitation rate, $CO_2$ content, and $H_2$ gas partial pressure). Major changes in nutrients are avoided, but instead a relatively constant nutrient feed concentration is maintained. An example of such regulation of fermentation parameters for a particular bacterial culture is illustrated in Example 19.

Preferably, the biological pathway is controlled to favor ethanol production and limit acetic acid production by first feeding excess $H_2$ to the reactor and then limiting cobalt in the nutrient medium as described above. At start-up, the limiting liquid phase nutrient cobalt is kept in excess to avoid acclimation to low nutrients concentration, a condition that can result in very poor culture performance and the loss of the cultures ability to produce product ratios greater than 1:1.

C. Oversupplying Hydrogen

In still another embodiment, the method for manipulating the biological pathways to favor ethanol production and limit acetic acid production involves feeding excess $H_2$ in the feed gas or limiting gaseous carbon which results in excess $H_2$, which is then used by the biological pathway. Preferably, the $H_2$ reducing gas is in excess relative to CO, and the excess $H_2$ causes the bacteria to produce a high ethanol to acetate ratio in the fermentation broth. If the ratio of the $H_2$ (moles of gas fed) to the sum of two times the CO (in moles of gas) converted and three times the $CO_2$ (in moles of gas) converted is greater than 1, the fermenter is carbon limited. The $H_2$ partial present in the exit gas is preferably greater than 0.4 atm.

Finally the ratio of $H_2$ partial pressure to $CO_2$ partial pressure must be greater than 3.0 to assure that sufficient $H_2$ is available to use all the $CO_2$. If the $CO_2$ partial pressure is greater than 0.1 atm, it is likely that growth has been otherwise limited. See, Example 20 for an illustration of this method step.

During start-up, the use of excess $H_2$ is favored over nutrient limitation, mainly because it is easier to control. The benefits of employing excess $H_2$ are that it avoids excess acetic acid production, which can lead to poor product ratios and potential acetic acid inhibition, as well as acclimation to low nutrient concentrations.

D. Oversupplying Carbon Monoxide

Another way of manipulating the components of the method involves oversupplying the reducing gas, CO, in the gaseous substrate for use in the pathway, which serves to directly lower the redox potential in the fermentation broth. Thus, according to this embodiment, the bioreactor is supplied with gaseous substrate comprising CO where the amount of CO present in the bioreactor is greater than the amount required to maintain the bacteria at a stable, steady state concentration that would fully utilize the CO provided. CO oversupply as a method of favoring ethanol production over acetic acid production when the specific rate of CO uptake (millimoles of CO per gram of cells (dry weight) in the reactor per minute, or mmol/g cell·min) is greater than 0.3. More preferably, this step involves a specific rate of CO uptake of greater than 0.5. This means that each cell on the average is utilizing CO in its metabolism at a rate of at least 0.3 mmol/g·min., or more ideally at a rate of at least 0.5 mmol/·min. Preferably, the CO is provided at a rate at which the CO uptake is from 0.3 to 2 mmol CO/gram cell (dry weight) of bacteria/minute. In another embodiment, the CO is provided at a rate of from 0.5 to 1.5 mmol CO/gram cell (dry weight) of bacteria/minute. In another embodiment, the CO is provided at a rate of about 1 mmol CO/gram cell (dry weight) of bacteria/minute. Example 24 provides an illustration of one embodiment of this method step.

This rate of CO uptake maintains ethanol production in preference to acetate production. If CO is supplied such that the dissolved CO in the fermentation broth is significant by gas pressure or extremely good mass transfer, the fermentation broth becomes more reduced. Oversupply of CO has two additional benefits. Excess CO may cause the CO cycle to operate at a faster rate, and if the Acetyl-CoA cycle is otherwise limited and cannot keep up with the CO cycle, reduced ferredoxin builds-up. CO may also slow down step 2 (production of the intermediate acetic acid) in the overall three-step method through substrate inhibition. This decreased rate of step 2 in relation to step 1 causes an excess of NAD(P)H, which leads to ethanol production in favor of acetic acid.

Although excess CO can result in increased ethanol production by directly reducing the redox potential of the fermentation broth, the presence of excess CO also inhibits growth by inhibiting the CO-dehydrogenase and therefore the uptake of $H_2$. The presence of excess CO unfortunately also results in poor $H_2$ conversion, which may not be economically favorable. The consequence of extended operation under substrate inhibition is poor $H_2$ uptake. This eventually causes cell lysis and necessary restarting of the reactor. Where this method has an unintended result of CO substrate inhibition (the presence of too much CO for the available cells) during the initial growth of the culture or thereafter, the gas feed rate and/or agitation rate is reduced until the substrate inhibition is relieved. An illustration of how to adjust the gas rate or agitation rate to accomplish this effect is illustrated in Example 21.

E. Additional Manipulating Steps

In addition to the major method enhancing steps described above, several method steps are desirably included in the ethanol production method.

1. Increasing Mass Transfer

One such additional embodiment involves ensuring that the mass transfer of the CO or $H_2$ from the gas feed to the liquid fermentation broth is faster than the ability of the bacteria to utilize the dissolved gases. For example, if a bioreactor containing *C. ljungdahlii* is fed CO, $CO_2$ and $H_2$ and is operated without limitation on nutrients (such as pantothenate or cobalt) or the presence of excess $H_2$, cell growth is limited by the amount of gas transferred into the liquid phase and the system produces acetic acid as the product. If the culture is fed a slight amount of CO or $H_2$ in excess of that required for culture growth, it produces ethanol. However, if too much gas is transferred into the liquid phase for the culture to use, substrate inhibition occurs, which can lead to culture upset and cell death. Thus, there is a very narrow range of operation with excess mass transfer. Example 22 provides an illustration of this method.

With reference to the Acetyl-CoA cycle, in order for the excess reduced ferredoxin to be produced, the CO cycle or the reduction of ferredoxin through hydrogenase must occur faster than the Acetyl-CoA cycle. The methods described herein limit the rate at which the organisms can utilize the dissolved gases by restricting the rate at which essential nutrients e.g., calcium pantothenate or cobalt, or other substrates, such as $CO_2$ gas, are available to the bacteria, or by providing excess substrate, $H_2$ or CO to the culture.

A theoretical rate of mass transfer, which is faster than the rate at which the bacteria can use substrate, even without other limitations, can be calculated. That rate, when achieved, is limited by the natural growth rate of the organism. Therefore, the most productive embodiment is where the mass transfer (gas flow rate or agitation rate) is faster than the rate at which the highest possible concentration of cells can utilize the substrate without any limitation. There would be a very narrow operating range since substrate inhibition could quickly cause cell death and a resulting by-product concentration which is toxic to the culture.

2. Supplying Excess CO And $H_2$

In another embodiment of a method of this invention, stability in the high ethanol concentration/limited acetic acid production is achieved in the methods which limit cobalt or calcium pantothenate, or provide an abundance of $H_2$ or CO. According to this step, as the culture uses the gaseous substrates CO, $H_2$ and $CO_2$ as the carbon and energy sources, CO and $H_2$ are supplied in slight excess. A slight excess of CO and $H_2$ is achieved by attaining steady operation and then gradually increasing the gas feed rate and/or agitation rate (10% or less increments) until the CO and $H_2$ conversions just start to decline. This is one means of avoiding mass transfer limitation, which favors acetic acid production, and supplying excess reduced ferredoxin in order to reduce NAD(P) to NAD(P)H and produce ethanol. If CO and $H_2$ are not supplied in slight excess, mass transfer limitation occurs, and the pathway is balanced. This results in poor ethanol to acetate product ratios (high acetate concentrations). High acetate concentrations can ultimately result in acetic acid inhibition, which limits the ability of the bacterium to take up $H_2$ and can eventually lead to culture failure.

Steps to avoid mass transfer limitation include an increase in the agitation rate or gas rate to transfer more CO and $H_2$ into the liquid phase, and thus return to the presence of a slight excess CO and $H_2$. If product inhibition occurs as a result of mass transfer limitation, it is necessary to increase the liquid feed rate to clear the acetic acid inhibition, by diluting to a lower resulting acetate concentration. Since increasing the medium feed rate would increase the μg pantothenate or cobalt/g-cell produced, this must be clone only briefly or the excess pantothenate or cobalt must be eliminated by adjusting the medium concentration or increasing the water feed rate.

3. Controlling Acetic Acid Product Inhibition

Where in the methods described above, acetic acid product inhibition can occur if too much molecular acetic acid, i.e., >2 g/L, accumulates in the bioreactor to allow cell growth and further ethanol production. Another manipulating step is used to avoid culture failure. One modification involves briefly increasing the liquid or aqueous feed rate to reduce the liquid phase concentration of inhibiting acetic acid to lower than 2 g/L. An illustration of this step for a particular culture in a reactor is demonstrated in Example 23.

4. Water Recycle Step

Still another optional method step for maintaining a stable culture which produces ethanol as the only product with no net acetic acid production in the methods of this invention involves adding water recycle from distillation back to the fermentation reactor (see, e.g., Example 15). As was noted earlier, water (containing up to 5 g/L acetate) recycle has the benefit of recycling the produced acetate back to the reactor so that no net acetic acid is produced. An equilibrium is thus established between the ethanol and acetate in the reactor. As a result, all CO, $CO_2$ and $H_2$ fed to the reactor and converted to products results in ethanol production, except for that used for culture maintenance.

5. Reducing Cell Density

Still another manipulating step useful in the method is to initiate periodic or continuous purging of bacterial cells from the bioreactor to reduce the cell concentration in the bioreactor. This manipulation serves to reduce the cell concentration to less than a stable, steady state cell concentration that utilizes all reducing gas or nutrient substrates in the bioreactor. By thus, altering the cell density, the production of ethanol is favored over the production of acetate in the bioreactor. See, e.g., Example 25.

6. Two Stage CSTR

One of the problems associated with ethanol production with medium limitation is the ability or tendency of the culture to eventually adapt to the limiting conditions and not continue to produce ethanol after several months of operation. Instead acetate eventually becomes the dominant product. This acclimation to low limiting nutrient concentrations results in a culture which produces more acetic acid than ethanol (ethanol to acetate product ratio of 1.0 or less), and yields low ethanol concentrations (sometimes as low as 1 g/L). Adaptation most likely occurs when the culture is not provided with sufficient nutrients during start-up, where growth rate is more important than ethanol production rate. Additionally, there is a danger that the culture can be acclimated to low limiting nutrient concentrations during steady state operation particularly as the limiting nutrient concentrations are adjusted downward to rid the reaction system of acetate.

To avoid this adaptation when using the pantothenate or cobalt limiting steps above, instead of allowing the culture to grow with the available nutrients, and the danger mentioned above, another modification of the method can be employed.

A two-stage CSTR system where primarily good culture growth occurs in the first stage on a slight excess of limiting nutrients (perhaps with accompanying acetic acid production), followed by a production stage where the culture from the first stage is now limited by the limiting nutrient and is used to produce high concentrations of ethanol, is another modification of the method. This modification enables the maintenance of a stable culture, which does not acclimate to reduced pantothenate or cobalt concentrations. This modification involves operating a two-stage CSTR, in which a growth reactor (Stage 1) to feed a production reactor (Stage 2) where the bulk of the ethanol production occurs.

The growth reactor is not operated with the nutrient limitation steps described above, so the culture is not as susceptible to acclimation to a limited condition.

Figure 2:
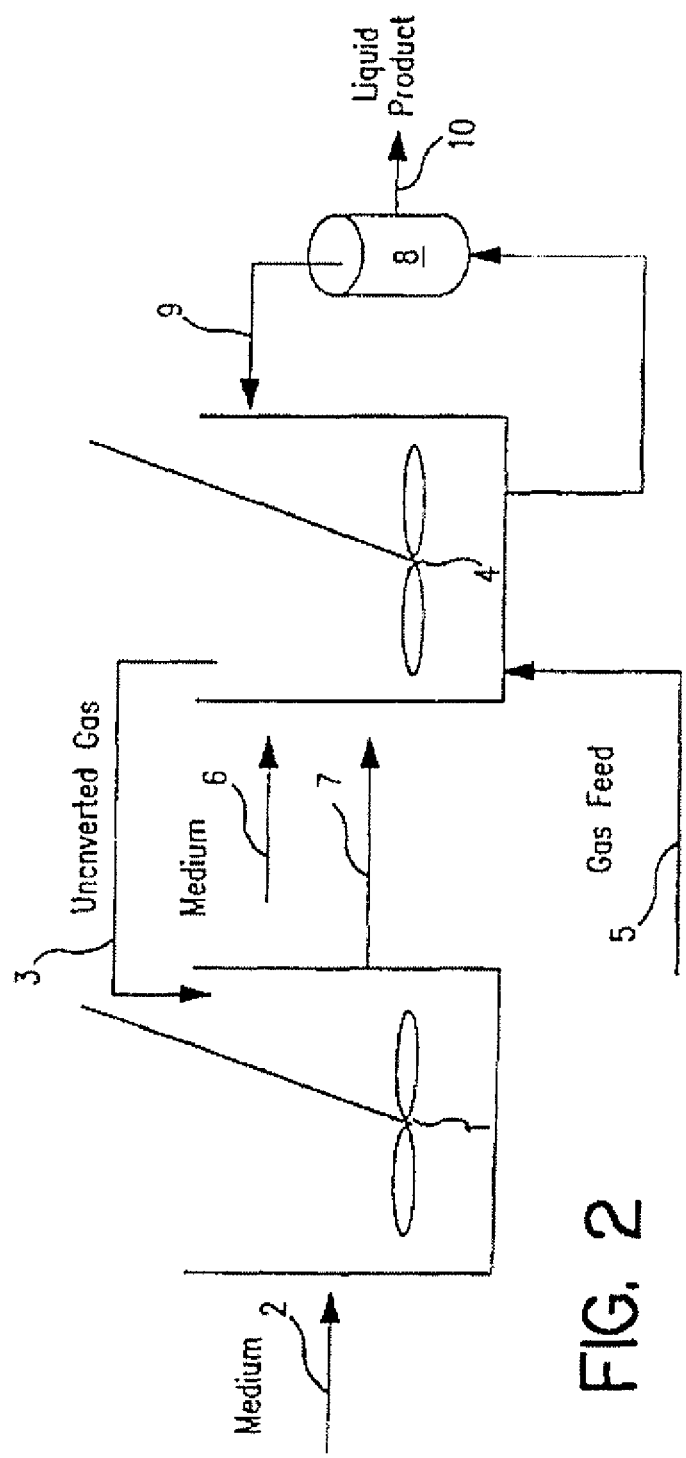
FIG. 2 is a schematic diagram of a two-stage, continuously stirred reactor (CSTR) system for improved culture stability. Growth stage CSTR 1 is fed liquid medium 2. Unconverted gas 3 from the Production Stage CSTR is fed to Growth Stage CSTR 1. Production Stage CSTR 4 is fed a fresh gas feed 5, and fresh medium feed 6 as well as culture feed 7 from Growth Stage CSTR 1. Cell recycle 8 is used to get the most production out of the cells 9 sent to Production Stage CSTR 4. Cells 9 are not recycled to the Growth Stage CSTR. Liquid Product 10 consisting of dilute ethanol in the fermentation broth is produced as the final distillation product, and is recovered as anhydrous ethanol as in FIG. 1.

A schematic diagram of this two-stage CSTR system is shown in FIG. 2, and the following description has reference to that figure. According to this embodiment, the Growth Stage is operated at a liquid retention time (LRT) of about 24 hours. The Growth Stage CSTR 1 is fed enough pantothenate or cobalt in the medium 2 to yield a healthy culture (and may produce some acetic acid as well). Thus, excess acetic acid is produced in the reactor, but with increased stability. This pantothenate or cobalt concentration is in excess of what would normally be fed to a single CSTR used to produce ethanol. The gas feed to this reactor is unconverted gas 3 from the Production Stage 4 and the liquid feed is fresh medium 2. The Growth Stage CSTR is operated without cell recycle. The purpose of this Growth Stage reactor is to provide a healthy culture for later ethanol production that does not acclimate to low pantothenate concentrations.

The Production stage reactor 4 is operated at a nominal LRT of less than 20 hours. This CSTR with cell recycle is fed a fresh gas feed 5, and may have low conversions. It is fed fresh medium feed 6 as well as culture feed 7 from the Growth Stage. Minimal pantothenate or cobalt is fed to this reactor since the excess from the Growth Stage is available. Cell recycle 8 is used in this reactor in order to get the most production out of the cells sent back to the reactor 9. The exit ethanol concentration in the liquid product 10 should be greater than 20 g/L. The features of the two-stage CSTR system include little change for acclimation to low pantothenate or cobalt concentrations; an overall LRT of less than or equal to 30 hours; an expected greater ethanol productivity and higher ethanol concentration than from a single CSTR of the same size.

7. Start-Up Modifications

Still other method steps, which are preferably utilized in the practice of this invention, involve cell production in the initial start-up of the fermentation culture. The start-up of a bioreactor fed CO, $CO_2$ and $H_2$ to produce ethanol and acetic acid is accomplished by batch inoculation from stock culture (Example 11) or by employing a continuous inoculum from an existing reactor as culture feed (Example 12). As noted earlier in the discussion of avoiding culture acclimation to low pantothenate or cobalt concentrations, the culture is most desirably brought up to a high cell concentration prior to limiting nutrients, but supplying excess $H_2$ to the culture. This rapid start-up avoids culture acclimation and yields good product ratios (high ethanol and low acetate concentrations). If the rapid start-up is not employed, poor product ratios can occur and the culture can acclimate to low liquid phase nutrient concentrations and require reactor reinoculation.

The reactor is started with a batch liquid phase (liquid medium is not initially fed continuously to the reactor), at low agitation rates (perhaps 400-600 rpm in a laboratory New Brunswick Scientific Bioflo® reactor) and at the desired pH. The liquid phase in the reactor thus consists of a batch of nutrient medium containing vitamins and salts, with a nominal concentration of limiting nutrient, either calcium pantothenate or cobalt (20 µg/L pantothenate or 75 ppb cobalt as an example). if continuous inoculum from an existing reactor is employed, batch liquid phase operation likely is not necessary. In this case, gas is fed continuously to the reactor during initial start-up at a slow rate. Ideally, the gas phase at start-up would be $CO_2$-free, $H_2$-abundant and the gas rate and agitation rate would be kept at low levels to avoid CO substrate inhibition.

An exemplary general start-up protocol for producing and sustaining commercially viable ethanol concentrations from CO, $CO_2$ and $H_2$ consists of three distinct phases: (a) initial start-up, where cell production is critical; (b) start-up where production rate becomes critical; and (c) steady state operation. Essentially, initial start-up is characterized by inoculation of a hatch liquid, with a nominal limiting nutrient, selected from cobalt (75 ppb) or calcium pantothenate (20 µg/L) at a desired pH (typically 4.5-5.5). To facilitate start-up, the gas feed rate and agitation rate are preferentially kept low, while $H_2$ is fed in excess. The cause of ethanol production during start-up is excess $H_2$; nutrient limitation occurs later. Thus, excess liquid nutrients are actually present during start-up to avoid unwanted culture acclimation to low nutrients. As the fermentation proceeds over a period of several hours after inoculation, $CO_2$ is produced and $H_2$ is consumed. The changes in these rates indicated that the agitation rate should be nominally increased slowly (perhaps by 200-300 rpm in a laboratory reactor, over a period of 2-3 days) to avoid mass transfer limitation.

This onset of $CO_2$ production occurs much more rapidly in systems employing continuous inoculation as opposed to batch inoculation from stock culture. However, if the agitation rate is increased too fast, CO substrate inhibition occurs. This procedure of watching $H_2$ conversion (or $CO_2$ production) while nominally increasing agitation rate occurs at a relatively rapid rate until the target agitation rate is reached. During this time of increasing agitation rate in batch liquid culture, cell production instead of product formation is of utmost importance.

Once the target agitation rate is reached (800-1000 rpm in laboratory New Brunswick Scientific Bioflo® reactor), the culture is allowed to steady to confirm $H_2$ uptake. The start-up shifts to a mode in which production rate becomes important. It is desirable to have CO conversions exceeding 80% and a high $H_2$ partial pressure in the exit gas (at least 0.55 atm) to assure ethanol production while limiting acetate and the free molecular acetic acid concentration. The liquid medium feed rate is then turned on (for systems having batch inoculation from stock culture) to initiate continuous liquid feed and the gas rate is increased in 10% increments toward the target flow rate. $H_2$ remains in excess to avoid excess acetic acid production. As the gas rate is increased, the liquid phase nutrients are limited (calcium pantothenate or cobalt), and the effect of such limitation is a small drop in $H_2$ conversion, at the target production.

At steady state operation, production of 15-35 g/L ethanol and 0-5 g/L acetate is reached. At this stage, small adjustments in limiting nutrients, liquid feed rates and gas feed rates are needed, and are chosen by one of skill in the art with resort to knowledge extant in the art as well as the teachings of this invention. If cell recycle is to be added to the method of ethanol production, it is added at this time along with an adjustment in gas rate (increase) and nutrient concentration (decrease).

The above described methods of continuously producing and maintaining high concentrations of ethanol with low by-product acetate concentrations under stable operating conditions enhance the use of the subject bacteria on a commercial scale for ethanol production. The steps outlined in the methods above overcome the limitations of utilizing the subject bacteria for commercial ethanol production from CO, $CO_2$ and $H_2$. Preferably the method employs a continuous bioreactor, although batch and fed-batch fermentation methods are also used, but are not likely to be economically viable for large-scale ethanol production.

The following examples illustrate various aspects, methods and method steps according to this invention. These examples do not limit the invention, the scope of which is embodied in the appended claims.

EXAMPLE 1

An Exemplary Method of the Present Invention

A synthesis or waste gas containing CO and/or $CO_2/H_2$ is continuously introduced into a stirred tank bioreactor containing a strain of *C. ljungdahlii*, along with a conventional liquid medium containing vitamins, trace metals and salts. One desirable nutrient medium is reported in Table 1 below.

During method start-up using a culture inoculum of 10% or less the reactor is operated with a batch liquid phase, where the liquid medium is not fed continuously to the reactor. The liquid phase in the reactor thus consists of a batch of nutrient medium with a nominal concentration of limiting nutrient, either calcium pantothenate or cobalt. Alternatively, a rich medium containing yeast extract, trypticase or other complex nutrients can also be employed.

Ideally, the gas phase at start-up is $CO_2$-free and contains excess $H_2$. The gas rate and agitation rate are kept at low levels (less than 500 rpm in a New Brunswick Scientific Bioflo® fermentation bioreactor) to yield CO and $H_2$ in slight excess, but at the same time, avoiding CO substrate inhibition. In a one-liter laboratory New Brunswick Scientific Bioflo® fermentation bioreactor, as an example, where the feed gas composition is 63% $H_2$, 32% CO and 5% $CH_4$, the agitation rate to initiate start-up is 400 rpm and the gas rate is 20 mL/min. The cause of ethanol production during start-up is excess $H_2$; limitation on nutrients occurs later. Thus, excess liquid nutrients (pantothenate, cobalt) are actually present during start-up to avoid unwanted culture acclimation to low nutrients.

As the fermentation proceeds over a period of several hours after inoculation, $CO_2$ is produced from the conversion of CO, and $H_2$ is consumed along with the $CO_2$, which is a signal to nominally increase the agitation rate to avoid gas mass transfer limitation. In the New Brunswick Scientific Bioflo® CSTR, the exit gas is 25% CO, 67% $H_2$, 2% $CO_2$, and 6% $CH_4$. If the agitation rate is increased too fast, CO substrate inhibition occurs, as evidenced by a decrease in methane concentration after an increase in agitation. Thus the agitation rate might typically be increased by 200 rpm in 24 hours. This procedure of monitoring $CO_2$ production (or $H_2$ conversion) while nominally increasing agitation rate occurs at a relatively rapid rate until the target agitation rate is reached. A typical target agitation rate in the New Brunswick Scientific Bioflo® fermentation bioreactor is 900 rpm. During this time of increasing agitation rate in batch liquid culture, cell production instead of product formation is of utmost importance. Thus, cell concentrations of about 1.5 g/L are attained, while typical product concentrations are 10 g/L ethanol and 2 g/L acetate from the batch culture.

Once the target agitation rate is reached, the system is allowed to grow to maximum $H_2$ uptake. It is desirable to have very high $H_2$ exit concentrations (typically >60%) to assure ethanol production while limiting acetic acid production. The liquid medium feed is then turned on (for systems having batch inoculation from stock culture) to initiate continuous liquid feed and the gas feed rate is increased toward the target flow rate. In the laboratory New Brunswick Scientific Bioflo® fermentation bioreactor the liquid feed rate is typically 0.5 ml/min, while the gas flow rate is increased by 10 to 15% every 24 hours toward a target rate of 125 mL/min.

It is important to provide excess $H_2$ in the feed gas to avoid excess acetic acid production. As the gas flow rate is increased, cell production increases until the reactor is eventually limited on liquid phase nutrients (calcium pantothenate or cobalt) as evidenced by a small drop in $H_2$ conversion, at the target productivity. In the New Brunswick Scientific BIOFLO® CSTR, this is recognized by a 10% drop in $H_2$ conversion at a target productivity of 20 g/L·day.

The production method and reactor system are then maintained at a steady state producing 15 to 35 g/L ethanol and 0 to 5 g/L acetate as products, with only occasional small adjustments in limiting nutrients, liquid rates and gas rate. Typical steady state conditions in the laboratory New Brunswick Scientific Bioflo® fermentation bioreactor without cell recycle, are a gas retention time (gas flow rate/reactor liquid volume) of 20 minutes, a liquid retention time (liquid flow rate/reactor liquid volume) of 30 hours and an agitation rate of 900 rpm, yielding CO conversions of 92% and $H_2$ conversions of 60% with pantothenate limitation.

In an embodiment of this method in which cell recycle is added to the reactor system, it is added at this time along with an adjustment in gas rate (increase) and nutrient concentration (decrease). With cell recycle in the New Brunswick Scientific Bioflo® CSTR, the gas retention time is typically 8 minutes, the liquid retention time is 12 hours, the cell retention time is 40 hours and the agitation rate is 900 rpm. These conditions typically yield a CO conversion of 92% and a $H_2$ conversion of 50% with pantothenate limitation.

EXAMPLE 2

Sample Analysis Via Gas Chromatography

To achieve and/or maintain proper productivity and ratio, a sample of the fermentation broth in the fermentation bioreactor must be periodically sampled. A sample greater than 1.5 mL of culture is taken from the culture in the bioreactor. The sample is placed in a microcentrifuge tube and the tube is placed in a Fisher Scientific Micro 14 centrifuge with necessary ballast for balancing. The sample is subjected to 8000 rpm for 1.5 minutes. A 0.500 mL sample of supernatant is placed into a 1.5 mL vial designed for use in a gas chromatograph autosampler. A 0.500 mL sample of an internal standard solution containing 5 g/L of n-propanol and 5% v/v, 85% phosphoric acid in deionized water. The phosphoric acid assures the all acetate is converted to acetic acid and is detected by gas chromatography.

One μl of the prepared sample is then injected by autosampler into a Hewlett-Packard 5890 Series II Gas Chromatograph equipped with a 007 FFA Quadrex 25 m×0.53 mm ID fused silica capillary column. The analysis is conducted with a helium carrier gas in split-flow mode with 66 mL/min split-flow and 7.93 mL/min injector purge. The column head pressure is set to 4 psig which yields a column carrier flow of 7 mL/min. The temperature program is 75° C. for 0.2 minutes, a ramp to 190° C. at a rate of 30° C./minute, and a hold time at 190° C. for 5.17 minutes. The resulting runtime is 8 minutes. The instrument is calibrated for ethanol (0 B 25 g/L), acetic acid (0-25 g/L), n-butanol (0-5 g/L) and butyric acid (0-5 g/L). Five standards, prepared from reagent grade materials, are used for the calibration. If the sample is outside the calibration range of concentration (e.g., >25 g/L ethanol), 0.250 mL of the sample and 0.250 mL of deionized water are placed into the vial with 0.500 mL of the internal standard and the dilution factor is included in the analysis.

EXAMPLE 3

Acid Production in a Laboratory CSTR with Cell Recycle

A New Brunswick Scientific Bioflo® laboratory fermentation bioreactor was operated with cell recycle using *Clostridium ljungdahlii*, strain ERI-2, ATCC 55380 for the production of acetic acid from CO, $CO_2$ and $H_2$. The gas feed contained 40% $H_2$, 50% CO and 10% $N_2$, and the gas retention time to the one-liter reactor was 7.7 to 8.6 minutes. Liquid medium containing vitamins, salts and trace elements was fed at a liquid retention time of 2.6 to 2.9 hours. The pH was 5.1 to 5.2, the agitation rate was 1000 rpm and the cell retention time was about 40 hours. Under these conditions of mass transfer limitation (and not nutrient limitation), the CO conversion was 94 to 98% and the $H_2$ conversion was 80 to 97%. The cell concentration was 4 to 8 g/L, and acetate was produced at 10 to 13 g/L. No ethanol was produced. Although the reactor was operated under mass transfer limitation (limited by the ability to transfer gas to the culture) and thus produced only acetic acid as the product, the parameters for ethanol production through pantothenate limitation, cobalt limitation or the presence of excess $H_2$ or CO were monitored to serve as comparisons for when ethanol is produced as the dominant product.

As shown in Table 2, the Ca-d-pantothenate fed per unit of cells produced was 1575 to 3150 micro-grams per gram of cells produced (μg/g-cell produced). Similarly the cobalt fed per gram of cells produced was 1734 to 3468 (μg/g-cell produced). The specific CO uptake rate was 0.35 to 0.61 mmol/g-cell·minute. The ratio of the moles of $H_2$ fed to the sum of two times the moles of CO converted and three times the moles of $CO_2$ converted was less than 0.46. Thus, none of the parameters were in the desired operating range for ethanol production by the culture.

It is realized that pantothenate and cobalt were fed in large excess to the reactor above when making acetic acid as the product under mass transfer limitation. That is, the pantothenate and/or cobalt levels could be decreased significantly and still be above the levels for pantothenate or cobalt limitation. To illustrate this, the medium fed to the 1-liter New Brunswick Scientific BIOFLO® fermentation bioreactor was modified to significantly decrease cobalt addition to a level that was just above the concentration of cobalt for cobalt limitation. The reactor again contained *C. ljungdahlii* strain ERI-2 for production of acetic acid from CO, $CO_2$ and $H_2$. The gas feed contained 55% $H_2$, 25% CO, 15% $CO_2$ and 5% $CH_4$ (reference gas), and the gas retention time was 7.5 to 8.0 minutes. Liquid medium containing salts, vitamins and trace elements was fed at a liquid retention time of 3.0 to 3.5 hours, and the cell retention time was 40 hours. The pH was 5.0 to 5.3 and the agitation rate was 900 to 1000 rpm. Under these conditions the CO conversion was 95 to 99% and the $H_2$ conversion was 94 to 98%. The cell concentration was 2.5 to 4.0 g/L and acetate was the only product at 10 to 14 g/L.

The Ca-d-pantothenate fed to the reactor per gram of cells was 2250 to 3600 μg pantothenate/g-cells produced. The cobalt fed per unit of cells produced was reduced to a range of 62.0 to 99.2 μg cobalt/g-cells produced. The specific CO uptake rate was 0.325 to 0.4 mmol/g-cell·minute. The ratio of $H_2$ fed to the sum of two times the CO converted and three times the $CO_2$ converted was 0.875.

EXAMPLE 4

Ethanol Production in Laboratory CSTRs with Pantothenate Limitation

A New Brunswick Scientific Bioflo® II laboratory fermentation bioreactor was operated as a straight through CSTR (without cell recycle) using *C. ljungdahlii*, strain C-01 ATCC 55988 for the production of ethanol from CO, $CO_2$ and $H_2$, limited on pantothenate. The gas feed to the reactor contained 63.3% $H_2$, 31.4% CO and 5.3% $C_2H_6$ (reference gas); fed at a gas retention time of 27 minutes. Liquid medium containing excess salts and trace elements and a limited supply of pantothenate was fed to the 1.55 liter reactor at a liquid retention time of 31.4 hours. The pH was 4.6 to 4.7, and the agitation rate was 650 rpm. Under these operating conditions the CO conversion was 98%, the $H_2$ conversion was 83% and the cell concentration was 1.5 to 2.0 g/L. Ethanol was produced at a concentration of 15 to 19 g/L, and acetate was produced at 1.5 g/L. The ethanol productivity ranged from 11.5 to 14.5 g/L·day.

In analyzing the parameters for ethanol production, pantothenate limitation was seen by operating with a pantothenate feed to cell production ratio of 17.7 to 23.6 μg pantothenate/g-cell produced. Compare this ratio to the 2250 to 3600 μg pantothenate/g-cell produced and 1575-3150 μg pantothenate/g-cell produced in Example 3 for acid production. The cobalt fed per unit of cells produced was 5000 to 6000 μg cobalt/g-cell produced, a level that is even greater than in Example 3 and assures no cobalt limitation. The specific CO uptake rate was 0.23 to 0.30 mmol/g-cell·minute. The ratio of $H_2$ fed to the sum of two times the CO converted and three times the $CO_2$ converted was 1.03, and the $H_2$ partial pressure in the exit gas was 0.55-0.64 atm. It is possible that either excess $H_2$ or limited pantothenate caused ethanol production.

Pantothenate limitation for ethanol production was also addressed in another New Brunswick Scientific Bioflo® II laboratory reactor operated with cell recycle using *C. ljungdahlii*, strain C-01 ATCC 55988. This reactor was fed gas containing 61.7% $H_2$, 30.6% CO and 5.2% $C_2H_6$ (reference gas) at a gas retention time of 12.3 minutes. Liquid medium containing a limited supply of pantothenate along with excess salts and trace elements was fed to the 2.4 liter reactor at a liquid retention time of 24.8 hours. Cell recycle was provided by employing a 0.2 μm hollow fiber membrane, and the cell retention time was 69 hours. The pH was 4.6, and the agitation rate was 650 rpm. Under these conditions the CO conversion was 90%, the $H_2$ conversion was 53% and the cell concentration was 2.5 g/L. The ethanol concentration was 18 g/L and the acetate concentration was 3 g/L. The ethanol productivity was 17.4 g/L·day.

In analyzing the parameters for ethanol production (Table 2), the ratio of pantothenate fed per unit of cells produced was 8.08 μg pantothenate/g-cell produced. Again, pantothenate limitation was assured by operating at a level far less than that required for acetate production. The cobalt fed per unit of cells produced was 3960 μg cobalt/g-cell produced. The specific CO uptake rate was 0.33 mmole/g-cell-minute. The ratio of $H_2$ fed to the sum of two times the CO converted and three times the $CO_2$ converted was 1.14, and the $H_2$ partial pressure in the exit gas was 0.60-0.65 atm. Excess $H_2$ could be a potential reason for ethanol production; however, the high $CO_2$ content in the exit gas (0.14 atm) shows that growth was limited by pantothenate.

In another experiment, *C. ljungdahlii*, strain ERI-2 was fed 1500 to 3600 μg pantothenate/g cells produced during acetic acid production from CO, $CO_2$ and $H_2$, a condition where the reactor was not limited on pantothenate (or any other limitation except for the ability to transfer gas to the culture), and no ethanol was found in the product stream.

During limitation on pantothenate for ethanol production from CO, $CO_2$ and $H_2$, *C. ljungdahlii*, strain C-01 was fed 8 to 24 μg pantothenate/g cells produced, while maintaining all other nutrients in excess. Under these conditions, strain CM I produced 15 to 19 g/L ethanol and 1.5 to 3.0 g/L acetate.

EXAMPLE 5

Ethanol Production in Laboratory CSTRS with Cobalt Limitation

A New Brunswick Scientific Bioflo® II laboratory fermentation bioreactor was operated as a straight through CSTR (with no cell recycle) using *C. ljungdahlii*, strain C-01, ATCC 55988 for the production of ethanol from CO, $CO_2$ and $H_2$ with cobalt limitation. The gas fed to the reactor contained 60% $H_2$, 35% CO and 5% $CH_4$ (reference gas), and was fed at a gas retention time of 14 minutes. Liquid medium containing excess salts, vitamins and trace metals (except for cobalt, which was limiting) was fed to the 2.5 L reactor at a liquid retention time of 40 hours. The pH was 4.9 and the agitation rate was 650 rpm. Under these conditions the CO conversion was 91%, while the $H_2$ conversion varied from 20 to 80%, but was nominally 55%. Ethanol was produced at 26 g/L, acetate was produced at 4 g/L and the cell concentration was 2.5 g/L. The ethanol productivity was 15.6 g/L·day.

In analyzing the parameters for ethanol production, the ratio of the pantothenate fed to the cell production was 15.2 μg pantothenate/g-cell produced. This level was quite low, such that cobalt limitation might not be assured in favor of pantothenate limitation. Cobalt limitation was seen by operating with 33.3 μg cobalt/g-cell produced, a level which is 100 times less than used in reactors without cobalt limitation. The ratio of the $H_2$ fed to the sum of two times the CO converted and three times the $CO_2$ converted was 0.94. The specific CO uptake rate was 0.37 mmole/g-cell·minute.

Cobalt limitation for ethanol production was also demonstrated in a CSTR with cell recycle using *C. ljungdahlii*, strain C-01 ATCC 55988. This experiment was run to demonstrate cobalt limitation in the presence of excess pantothenate, in contrast to the previous reactor in this example. The New Brunswick Scientific Bioflo® 2000 laboratory fermentation bioreactor with a 0.2 μm hollow fiber membrane for cell recycle, was fed gas containing 60% $H_2$, 35% CO and 5% $CH_4$ (reference gas) at a gas retention time of 5 minutes. Liquid medium containing excess salts, vitamins and trace metals (again, except for cobalt which is limiting) was fed to the 1.2 liter reactor at a liquid retention time of 16 hours. The pH was 5.1 and the agitation rate was 825 rpm. The cell retention time in this CSTR with hollow fiber for cell recycle was 40 hours. Under these conditions the CO conversion was 83%, the $H_2$ conversion was 50% and the cell concentration was 4.2 g/L. The ethanol concentration was 18 g/L and the acetate concentration was 4 g/L. The ethanol productivity was 27 g/L·day.

In addressing the parameters for ethanol production in this reactor (Table 2), the ratio of pantothenate fed to cell production was 85.7 μg pantothenate/g-cells produced, a level which is 5.5 times greater than in the previous reactor in this example. Cobalt limitation was seen by operating with 47.6 μg cobalt/g-cells produced. The ratio of $H_2$ fed to the sum of two times the CO converted and three times the $CO_2$ converted was 1.03, and the $H_2$ partial pressure in the exit gas was 0.60 atm. Again, excess $H_2$ could be a potential reason for ethanol production; however, the high $CO_2$ content in the exit gas (0.1-0.15 atm) shows that growth was limited by cobalt. The specific CO uptake was 0.50 mmol/g-cell·minute.

EXAMPLE 6

Ethanol Production in Laboratory CSTRs when Operating with Excess CO Present

A high pressure AUTOKLAV™ reactor (Buchi) was operated as a CSTR with culture circulation and cell recycle using *C. ljungdahlii* strain C-01 for the production of ethanol from CO, $CO_2$ and $H_2$ in the presence of excess CO for a period of 50 hours. The reactor was operated at 25 prig and fed gas containing 57% $H_2$, 36% CO and 6% $C_2H_6$. The gas retention time was variable, but was nominally 3.0 minutes. Liquid medium containing excess salts, vitamins (including pantothenate) and trace metals was fed to the 600 mL reactor at a liquid retention time of 8.2 hours. The cell retention time, obtained by passing the reactor effluent through a ceramic hollow fiber filter, was 18.5 hours. The pH was 4.5, the agitation rate was 450 rpm and the liquid recirculation rate was 0.4 to 0.5 gpm. Under these conditions, the gas conversions were variable, but the CO conversion was nominally 72% and the $H_2$ conversion was nominally 12%. The cell concentration was 2.7 g/L. Ethanol was produced at 9.9 g/L and acetate was produced at 2.6 g/L. The ethanol productivity was 29.0 g/L·day.

In analyzing the parameters for ethanol production, the ratio of the pantothenate fed to the cell production was 97 μg pantothenate/g-cell produced. This level is sufficiently high to assure that pantothenate was not limiting. The ratio of cobalt fed to the cell production was 836 μm cobalt/g cell produced, again a level that assures that cobalt was not limiting. The ratio of the $H_2$ fed to the sum of two times the CO converted and three times the $CO_2$ converted was 1.09, and the $H_2$ partial pressure was 1.6 atm. The high $CO_2$ content in the exit gas (0.5 atm) assures that excess $H_2$ did not cause ethanol production. The specific CO uptake rate was 1.34 mmol/g-cell·min., a level that assures excess CO as a method of producing ethanol.

The technique of using excess CO for ethanol production was also demonstrated in another experiment with *C. ljungdahlii*, strain C-01 in the AUTOKLAV™ reactor (Buchi) system, again with cell recycle and with culture circulation, for a period of 24 hours. In this experiment the 600 mL reactor was fed gas containing 15.8% $H_2$, 36.5% CO, 38.4% $N_2$ and 9.3% $CO_2$ at a 1.4 minute gas retention time. The reactor pressure was maintained at 40 psig. Liquid medium containing excess salts, vitamins and trace metals was fed at a liquid retention time of 4.8 hours, and the cell retention time, obtained by passing effluent through a ceramic hollow fiber filter, was 19.2 hours. The pH was 4.5, the agitation rate was 1000 rpm and the liquid recirculation rate was 0.4 to 0.5 gpm. Under these conditions, the CO conversion was 71.6% and the $H_2$ conversion was 11.8%. The cell concentration was 7.1 g/L, ethanol was produced at 12.0 g/L and acetate was produced at 2.7 g/L. The ethanol productivity was 60 g/L·day.

In analyzing the parameters for ethanol production (Table 2), the ratio of pantothenate fed to the cell production was 294 μg pantothenate/g-cell produced. This level is far in excess of the minimum level required to cause ethanol production due to pantothenate limitation. The rate of cobalt fed to the cell production was 735 μg cobalt/g cell produced, again a level that ensures the cobalt was fed in excess. The ratio of $H_2$ fed to the sum of two times the CO converted and three times the $CO_2$ converted was 0.3. The CO uptake rate was 0.67 mmol/g cell·min., a level that again assures that excess CO is available as the method of causing ethanol to be produced.

EXAMPLE 7

Ethanol Production with Excess $H_2$ Present

A New Brunswick Scientific Bioflo® laboratory fermentation bioreactor was operated as a straight through CSTR (without cell recycle) using *C. ljungdahlii*, strain C-01 ATCC 55988 for the production of ethanol from CO, $CO_2$ and $H_2$ in the presence of excess $H_2$. The gas feed to the reactor contained 77% $H_2$, 19% CO and 4% $CH_4$ (reference gas), fed at a gas retention time of 30 minutes. Liquid medium containing excess salts, vitamins and trace elements was fed to the reactor at a liquid retention time of 36 hours. The pH was 5.0 and the agitation rate was 1000 rpm. Under these operating conditions the CO conversion was 97-99% and the $H_2$ conversion was 60-80%. The cell concentration was 0.8-1.0 g/L, the ethanol concentration was 10 g/L and the acetate concentration was 3.3 g/L. The ethanol productivity was 6.7 g/L·day.

In analyzing the parameters for ethanol production, the pantothenate feed to cell production ratio was 900-1125 μg pantothenate/g cell produced, thus assuring excess pantothenate was present. Similarly, the cobalt feed to cell production ratio was 991-1239 μg cobalt/g cell produced, again assuring that excess cobalt was present. The specific CO uptake rate was 0.28-0.35 mmol/g cell min, a level such that excess CO was not causing ethanol production. The ratio of the moles of $H_2$ fed to the sum of 2 times the moles CO converted and three times the moles $CO_2$ converted was 1.96, a ratio that is above 1.0, the level where excess $H_2$ is present and thus could be controlling ethanol production. The $H_2$ partial pressure in the exit gas was 0.70-0.87 atm, and the ratio of the $H_2$ partial pressure to $CO_2$ partial pressure in the exit gas was 65. Thus, the reactor was producing ethanol due to the presence of excess $H_2$.

In a second experiment, a high pressure AUTOKLAV™ reactor (Buchi) was operated as a CSTR with culture circulation and cell recycle using *C. ljungdahlii*, strain C-01 for the production of ethanol from CO, $CO_2$ and $H_2$ in the presence of excess $H_2$. The gas feed to the reactor contained 81% $H_2$, 16% CO and 3% CH4 (reference gas), fed at a gas retention time of 2.21 minutes. Liquid medium containing excess salts, vitamins and trace elements was fed to the reactor at a liquid retention time of 8.97 hours. The cell retention time was 22.7 hours, the pH was 4.5 and the agitation rate was 800 rpm. Under these operating conditions the CO conversion was 91.5% and the $H_2$ conversion was 43.4%. The cell concentration was 5.5 g/L and the acetate concentration was 2.85 g/L. The ethanol productivity in the reactor was 215-240 g/L·day.

In analyzing the parameters for ethanol production, the pantothenate feed to cell production rate was 46 μg pantothenate/g cell produced, a level that may indicate pantothenate limitation. The cobalt feed to cell production ratio was 460 μg cobalt/g cell produced, a level which assures that cobalt was not limiting. The specific CO uptake rate was 1.68 mmol/ g·cell·min, a level that could indicate that excess CO were present if it were not for the high $H_2$ uptake rate of 4.14 mmol/g·cell·min, which indicates that substrate inhibition to the $H_2$ conversion was not occurring. The ratio of the moles of $H_2$ fed to the sum of two times the moles CO converted and three times the moles $CO_2$ converted was 5.67, a rate that is far above the required ratio of 1.0 for excess $H_2$ to be present. The $H_2$ partial pressure in the exit gas 2.61 atm, and the rate of $H_2$ partial pressure to $CO_2$ partial pressure in the exit gas was 10.9. The reactor was thus producing ethanol as a result of the presence of excess $H_2$.

A summary comparison of method parameters and results for Examples 3 through 7 is shown in Table 2 below.

EXAMPLE 8

Product Shift In *C. Ljungdahlii* Strains ERI-2, C-01 and PETC Using Medium Formulations The methods of this invention can be applied to any of the *C. ljungdahlii* strains. Results from medium manipulation experiments employing strains ERI-2, C-01 and PETC are shown in Table 3 below. The purpose of these experiments was to demonstrate that each of the strains can be shifted from acetic acid production to ethanol production merely by manipulating the medium. Thus, a culture was fed excess nutrients (including pantothenate and cobalt) in order to produce acetic acid as the dominant product, and then limited on pantothenate or cobalt to produce ethanol as the dominant product. It should be emphasized that the only purpose of these experiments was to demonstrate that medium manipulation can result in product shift for each of the strains. Thus, attaining high product concentrations and productivities was not a focus of these experiments.

The reactor was operated as a straight through CSTR (no cell recycle) for each of the culture experiments. The gas retention time was nominally set at 50 minutes, the liquid retention time was nominally set at 40 hours and the agitation rate was nominally set at 1000 rpm. These conditions were chosen to allow comparisons of the strains, but not to achieve high productivities.

As noted in Table 3, strain ERI-2 was subjected to five changes in medium which shifted the products back and forth from acetic acid as the dominant product to ethanol as the dominant product. Both pantothenate limitation and cobalt limitation were demonstrated for ethanol production by this strain. Strain C-01 was shifted three times using medium manipulation, again with both pantothenate limitation and cobalt limitation demonstrated as the mechanism for ethanol production. Strain PETC was shifted only once, with ethanol production due to cobalt limitation. Each of the strains showed higher $H_2$ conversions when producing acetic acid, rather than ethanol, as the dominant product. This occurs because acetic acid is produced under mass transfer limitation (limiting the amount of gas to the culture), whereas ethanol is produced when limiting nutrients, and thus excess gas is supplied which can negatively affect gas conversion. Small amounts of acetate are always present in the product stream when the dominant product is ethanol. However, when acetic acid is the dominant product, ethanol is usually not present in measurable concentrations. In shifting dominant products from ethanol to acetic acid by nutrient manipulation, it was shown that it was very difficult to remove all traces of ethanol. Complete removal of ethanol occurred only after several weeks of continued operation on acetic acid enhancing medium.

EXAMPLE 9

Steady State Operation with and Without Cell Recycle

The ultimate commercial goal of producing ethanol from CO, $CO_2$ and $H_2$ is to achieve high steady state concentrations of ethanol, while at the same time, obtaining high ethanol to acetate product ratios and high productivity. Steady state data for the production of ethanol from CO-rich gas containing 20% $H_2$, 65% CO, 10% $CO_2$ and 5% $CH_4$ using *C. ljungdahlii*, strain C-01 in a straight through CSTR (no cell recycle) are shown in Table 4. In the table, GRT refers to the gas retention time (ratio of liquid volume to inlet gas flow rate), LRT refers to the liquid retention time (ratio of liquid volume to liquid flow rate), and XRT refers to the cell retention time (average amount of time cells spend in the reactor). As is noted in the Table 4, ethanol concentrations of 17.5 to 33 g/L were obtained, and the ethanol productivity ranged from 14.4 to 21.1 g/L·day.

Similar results are shown for ethanol production from gas that is not as rich in CO. The gas used in the experiment using *C. ljungdahlii* C-01 without recycle, for which results are reported in Table 5, contains 16% $H_2$, 27% CO, 6% $CO_2$, and 51% $N_2$. Ethanol concentrations ranging from 11 to 26 g/L were obtained with this gas, with 2.0 to 5.0 g/L acetate present as a secondary product. The ethanol productivity ranged from 11.1-20.1 g/L·day.*The cell concentration is based upon dry cell weight in Table 5.

Finally, steady state data for the conversion of gas containing 50% $H_2$, 45% CO and 5% $CH_4$ in a CSTR with cell recycle using *C. ljungdahlii* O-52 (ATCC Accession No. 55989) are shown in Table 6 below. Ethanol concentrations of 18 to 23.5 g/L and acetate concentrations of 3.0 to 5.7 g/L were attained. The ethanol productivity ranged from 21.1 to 39.0 g/L·day.

EXAMPLE 10

High Ethanol Productivity in a CSTR with Cell Recycle and Pressure

A high pressure AUTOKLAV™ reactor (Buchi) was operated as a CSTR with culture circulation and cell recycle using *C. ljungdahlii*, strain C-01 for the production of ethanol from CO, $CO_2$ and $H_2$. The reactor was operated at 30 psig and fed gas containing 62% $H_2$, 31% CO and 5% $C_2H_6$. The gas retention time was 1.14 min (atmospheric pressure basis), with an actual gas retention time of 3.5 min. Liquid medium containing excess salts, vitamins and trace metals was fed to the 600 mL reactor at a liquid retention time of 3.6 hours. The pH was 4.5 and the agitation rate was 825 rpm. Under these conditions, the cell concentration was 8 g/L, the CO conversion was 90% and the $H_2$ conversion was 40%. The product stream contained 20 g/L ethanol and 2.75 g/L acetate. The ethanol productivity was 150 g/L·day.

In another high pressure AUTOKLAV™ reactor (Buchi) operated as a CSTR with culture circulation and cell recycle using *C. ljungdahlii*, strain C-01, the reactor was operated at 6 atm (75 prig) and fed syngas containing 55% $H_2$, 30% CO, 5% $CH_4$ and 10% $CO_2$. The gas retention time was 1 min (atmospheric pressure basis), with an actual gas retention time of 6.0 min. Liquid medium containing excess salts, vitamins and trace metals was fed to the reactor at a liquid retention time of 1.62 hr. The cell retention time was 24 hr, the pH was 4.5 and the agitation rate was 800 rpm. Under these conditions, the cell concentration was 2.0 g/L, the CO conversion was 95% and the $H_2$ conversion was 60%. The product stream contained 25 g/L ethanol and 3 g/L acetate. The ethanol productivity was 369 g/L·d.

EXAMPLE 11

Start-Up From Stock Culture with Excess $H_2$ Present

Start-up using a batch inoculum from stock culture ensures a healthy inoculum free from contaminants, but is not always successful as an inoculation procedure because of the rather low cell density employed, especially if the method parameters such as gas rate and agitation rate are pushed upward too rapidly just after inoculation.

Start-up using batch inoculum from stock culture is discussed in this example. To prepare the stock cultures for inoculation of the reactor, cultures of *C. ljungdahlii*, strain C-01 (ATCC Accession No. 55988) were grown up in 150 mL serum bottles on CO, $CO_2$ and $H_2$ in a rich medium containing 1 g/L yeast extract and 1 g/L trypticase, in salts and vitamins. The vitamin concentration employed was 0.4 mL/L medium of an aqueous solution containing 50.5 mg/L. calcium pantothenate, 20.6 mg/L d-biotin and 50.6 mg/L thiamine HCl. Bottles were incubated at 37° C. in a shaker incubator. The cultures were grown to the exponential growth phase, as determined by visual inspection. With each inoculation, approximately 90 mL of stock culture were transferred from serum bottles to 1 liter of medium, representing 9% by volume inoculation. A successful inoculation is described below. The outlined procedure can be repeated several times to obtain a successful inoculation.

In obtaining a successful inoculation, 90 mL/L of inoculum were added to a 1 liter batch of basal medium (shown in Table 1) containing 0.4 mL/L vitamins and salts (t=0). The agitation rate was 240 rpm, the pH was 5.3, the temperature was 38.5° C. and the gas retention time (continuous gas flow) was 110 minutes. The gas feed contained 62% $H_2$, 31% CO and 7% $C_2H_6$. After 13 hr (t=13 hr) some CO conversion was noted, and at t=23 hr the agitation rate was increased from 240 rpm to 300 rpm. The gas retention time was decreased to 100 minutes at t=27 hr, and a further decrease in gas retention time was made at t=46 hr. The agitation rate was also increased in 100 rpm increments at t=28 hr, 59 hr, 72 hr and 85 hr.

By t=110 hr, the system was operating with a gas retention time of 80 minutes and an agitation rate of 600 rpm. The cell concentration was 0.5 g/L and the CO conversion was 35%. There was still no $H_2$ conversion, but small amounts of ethanol and acetate (~1 g/L each) had accumulated in the batch culture broth. The efforts up until this time emphasized cell growth in the reactor.

Medium flow using the same concentrations as in basal medium was started at a rate of 0.4 mL/min at t=120 hr. A program of nominal increases in gas rate, agitation rate and medium rate was then initiated while carefully maintaining the system under excess $H_2$. By t=210 hr, the ethanol concentration was 17 g/L, the acetate concentration was 1 g/L, the cell concentration was 1.6 g/L, the CO conversion was nearly 100% and the $H_2$ conversion was 90%. The ethanol productivity reached 11.4 g/L·day.

A program of gradual gas rate increases was again started. Concurrent vitamin (see Table 1) increases were made to bring the vitamin addition rate to 0.7 mL/L medium. By t=610 hr, the reactor was producing 20 g/L ethanol and about 2 g/L acetate. The CO conversion was nearly 100% and the $H_2$ conversion was 85%. The ethanol productivity reached 14 g/L·day.

EXAMPLE 12

Start-Up Using Inoculum From Existing CSTR

The start-up of a CSTR using continuous inoculum from an existing CSTR is much faster and is more dependable than a start-up from batch bottles of stock culture. A CSTR containing Isolate *C. ljungdahlii*, strain C-01 (ATCC Accession No. 55988), that had nearly ceased ethanol production and was producing 2-3 g/L ethanol, 7-8 g/L acetate and about 0.3 g/L butanol as the liquid phase products, was restarted using a continuous inoculum from an existing CSTR.

The CSTR from which the inoculum was taken was producing about 17 g/L ethanol and 1-2 g/L acetate, while operating at a gas retention time of 25 minutes, a liquid retention time of 32 hours, an agitation rate of 650 rpm, a temperature of 38.5° C. and pH 4.66. The cell concentration was 1.7 g/L, the CO conversion was essentially 100% and the $H_2$ conversion was 85%.

Continuous inoculum addition was started (t=0), and at this time, the agitation rate was reduced to 500 rpm and the gas retention time was set at 38 minutes. Effluent from the productive reactor (0.5 mL/min) served as the continuous inoculum for the CSTR being inoculated, with continuous inoculation occurring over a period of several hours. By t=5 hr (5 hr after the onset of continuous inoculation), gas conversion was noted, and the agitation rate was increased to 700 rpm. The continuous inoculum was turned off at t=28 hr. The gas conversions improved steadily, allowing steady increases in gas rate (lowered gas retention times) and an agitation rate increase to 750 rpm. By t=30 hr, the CO conversion was 95% and the $H_2$ conversion was 80%. The ethanol concentration was 13 g/L and acetate concentration was 1.5 g/L, and it steadied at 1.4 g/L for well over 100 hours. During this time period, the ethanol productivity was 10 to 15 g/L·day.

EXAMPLE 13

Recovery From Severe Method Upset

A CSTR with cell recycle containing *C. ljungdahlii*, strain C-01 being continuously fed gas and liquid nutrients and producing 15-35 g/L ethanol and 0-5 g/L acetate at a steady state (e.g., Example 1) is upset due to unforeseen changes in method conditions, e.g., mechanical problems in the reactor. Upset to the reactor system can either be minor, such as a brief increase in the gas rate which causes short-term substrate inhibition, or major, such as a longer term increase in the gas rate which eventually leads to increased acetic acid production and more severe molecular acetic acid product inhibition.

Short-term upsets are easily corrected by merely readjusting the upset parameter (for example, lowering the gas rate to its original level) and monitoring the progress of the reactor to assure that the upset has not led to a longer-term problem.

However, acetic acid product inhibition is a more severe problem. If excess molecular acetic acid is produced by the culture as a result of long term substrate inhibition, excess nutrient addition, $CO_2$ accumulation or mechanical problems of many types, the problem that led to the excess acetic acid must first be corrected. The excess acetic acid, which quickly leads to product inhibition, is then cleared from the system by increasing the liquid rate to wash the acetic acid (and unfortunately ethanol) from the system. Once the acetate level is below 3-5 g/L, the liquid rate is reset and the reactor is placed back under either excess $H_2$ feed, or vitamin or cobalt limitation (with or without cell recycle). Bringing the reactor back involves reducing the gas rate to avoid substrate inhibition and/or agitation rate before cell washout and lysis takes place. The agitation rate or gas rate is then increased, as described in Example 1.

In one specific example, a CSTR with cell recycle containing *C. ljungdahlii*, strain C-01 that was producing ethanol and acetic acid from CO, $CO_2$ and $H_2$ began producing acetic acid in response to a mechanical problem. The 2100 mL reactor was fed gas containing 62% $H_2$, 31% CO and 7% $C_2H_6$ at a gas retention time of 15 minutes, and was operating with an agitation rate of 600 rpm and a pH of 4.86. The liquid retention time was 23 hours and the cell retention time was 68 hours. B-vitamin solution (an aqueous mixture of 50.5 mg/l calcium pantothenate, 20.6 mg/L d-biotin and 50.6 mg/L thiamine HCl) was present in the liquid nutrient medium containing salts and vitamins at a concentration of 0.4 mL vitamin solution per liter of medium (see Table 2). The ethanol concentration fell to 7 g/L, while the acetate concentration rose to 7 g/L, conditions that are neither stable for operating the reactor nor economical for ethanol production. The cell concentration was 2.4 g/L, the CO conversion was 85% and the $H_2$ conversion was 25%.

The strategy used in recovering the reactor consisted of first dramatically reducing the gas feed rate to the reactor, followed by gradual recovery of the reactor in the presence of excess $H_2$. The liquid rate to the reactor was not reduced to clear product inhibition in this example because the acetate concentration was not exceedingly high. Instead, the acetate concentration was allowed to more gradually drop to non-inhibiting levels with the reduction in gas flow rate and subsequent operation in the presence of excess $H_2$. The specific procedure in recovering the reactor is discussed below.

Cell recycle was turned off and the gas rate was dramatically reduced by 70% to a gas retention time of 62 minutes, while only slightly adjusting the liquid retention time from 23 to 30 hours (t=0). The vitamin concentration in the medium was not changed. With this change in gas rate the CO conversion increased to 98% and the $H_2$ conversion increased to 80%. More importantly the system had excess $H_2$ present, as evidenced by the decrease in $CO_2$ in the outlet gas from 19 to 5%. With the onset of excess $H_2$, the acetate concentration fell while the ethanol concentration increased. At t=66 hr (66 hr after turning off cell recycle), for example, the acetate concentration had fallen to 4 g/L and the ethanol concentration had risen slightly to 7.5 g/L.

The presence of excess $H_2$ (and the lowered acetate concentration) permitted subsequent increases in gas rate, first slowly and then at a faster rate. By t=215 hr the gas retention was 29 minutes, the ethanol concentration was 12 g/L and the acetate concentration was 3 g/L. The ethanol productivity was 8 g/L·day. $CO_2$ was present in the outlet gas at 6%, the CO conversion was 98% and the $H_2$ conversion was 80%. By t=315 hr, the ethanol concentration was 16 g/L and the acetate concentration was 4 g/L, again with good gas conversions, and a gas retention time of 20 minutes. The ethanol productivity was 11 g/L·day. By t=465 hr, the ethanol concentration had reached 20 g/L, with 3.5 B 4 g/L acetate also present. The ethanol productivity was 16 g/L·day. The gas retention time had been dropped to 16 minutes, with CO and $H_2$ conversions of 95 and 73%, respectively. These conditions were maintained for nearly 200 hours of continuous operation, demonstrating that the reactor system had recovered its ability to produce ethanol and had essentially retained the previous operating conditions.

EXAMPLE 14

Ethanol Production Method with Oversupply of CO

A simple experiment was performed in a continuous high pressure stirred tank reactor with cell recycle to demonstrate the shift from acetic acid production to ethanol production due to the presence of high CO concentrations. Prior to this experiment the reactor containing *C. ljungdahlii*, strain C-01 was operated at a pressure of 20-25 psig and fed gas containing 57% $H_2$, 36% CO and 7% $C_2H_6$. The gas retention time was less than 2 minutes, the liquid retention time was 38 hours, the cell retention time was 28 hours, the agitation rate was 600 rpm and the temperature was 38° C. Under these conditions the CO conversion was variable and averaged 85%, and the $H_2$ conversion was variable and averaged 20%. The cell concentration was about 2.5 g/L, and the product stream contained 9 g/L ethanol and 3 g/L acetate.

As a first step in preparing for the test, the gas retention time was increased in order to ensure that excess CO was not present. The pressure was maintained at 23-24 psig. The pH was followed long enough to ensure that it was stable in the normal operating range of 4.5-4.6. Pure CO was then blended with the regular feed gas to yield a gas feed of 47% $H_2$, 47% CO and 6% $C_2H_6$ at a gas retention time of 2.3 minutes. The reactor pH, exit gas composition, and product stream were then monitored with time.

Table 7 shows the pH changes and product compositions with time after the addition of extra CO to the system. Thirty minutes after the CO addition, the reactor pH had increased to 5.25 and the culture had shifted 1.54 g/L (0.0257 mole/L) acetate to 1.12 g/L (0.0243 mole/L) ethanol. The pH increase occurred as a result of the free acetic acid being converted to ethanol. Accompanying this change was a decrease in CO conversion from 91% to 71%. In decreasing the culture circulation rate from 0.4 gpm to 0.15 gpm, the reactor pH fell, but the ethanol and acetate concentrations held.

Fifty minutes after CO introduction the ethanol concentration was 11.29 g/L and the acetate concentration was 1.75 g/L. At this time, the excess CO was turned off and the ethanol concentration and pH began to fall, and the acetate concentration began to rise. The decrease in pH was due to the conversion of ethanol to molecular acetic acid. The ethanol-acetic acid shift through oversupply of CO is thus reversible.

EXAMPLE 15

Water Recycle to Minimize Acetate Production

The recycle of method water back to the fermentation bioreactor after distillation to recover ethanol is essential to minimize effluent production, and to maximize the yield of ethanol from the reactor, and to limit the acetic acid production. Distillation has been found to be the most economical method for concentrating 15-35 g/L ethanol obtained from the reactor to 95% ethanol. Adsorption with molecular sieves is then used to further concentrate the ethanol to the desired concentration. In performing the distillation, 95% ethanol in water is produced as the overhead product. Water is generated as the bottoms product during distillation. The bottoms product contains acetic acid from the reactor produced during fermentation (3-5 g/L acetate) and any nutrients not used up during fermentation or destroyed by the heat of distillation, such as trace metals and other minerals. The recycle of nutrients minimizes the quantity of effluent that must be treated as well as the quantity of nutrients that must be subsequently added to the fermentation bioreactor. The recycle of acetate prevents the formation of further acetic acid by establishing equilibrium between the ethanol and acetic acid. Thus, no net acetic acid is produced with water recycle. Recycle of more than 3-5 g/L acetate can result in acetic acid inhibition in the reactor. Thus, as a result of water containing acetate recycle, the substrate CO, $CO_2$ and $H_2$ can be converted to ethanol as the only product.

Table 8 shows results for the fermentation of gas containing 50% CO, 45% $H_2$ and 5% $CH_4$; using *C. ljungdahlii*, strain O-52 with water recycle. In these experiments, the permeate from hollow fiber filtration used for cell recycle was sent to distillation. After removing ethanol, the water was filtered with a 0.2 micron filter to remove any precipitated by-products. The fraction of water recycled compared to the total water (as medium) fed to the reactor in these experiments ranged from 25-100%. The experiment with 100% water recycle lasted for nearly 500 hours or about 20 liquid retention times. As is noted in the results with 100% water recycle, no net acetic acid was produced. In fact, a small amount of acetic acid was eventually consumed. The ethanol productivity ranged from 12 to 27 g/L·day.

EXAMPLE 16

Two-Stage CSTR System with Pantothenate Feed to the Growth Stage

The proper pantothenate feed to the growth stage is a variable that must be optimized. Typical results from a Growth Stage Reactor using *C. ljungdahlii* C-01 were described in Examples 11 and 12, with the exception that a bit more acetic acid would be produced in this reactor since additional pantothenate or cobalt is fed to the Growth Stage to ensure a healthy and stable culture. The vitamin concentration employed was 0.7-0.8 mL/L medium of an aqueous solution containing 50.5 mg/L calcium pantothenate, 20.6 mg/L d-biotin and 50.6 mg/L thiamine HCl. The Production Stage CSTR with cell recycle is fed effluent from the growth stage reactor and produces ethanol as the predominant product. The pantothenate concentration fed to this reactor is much lower than in the Growth Stage, only 0.1-0.2 mL total vitamins/L medium of the aqueous solution containing 50.5 mg/L calcium pantothenate, 20.6 mg/L d-biotin and 50.6 mg/L thiamine HCl. The gas retention time in this Production Stage was 11-30 minutes, the liquid retention time was about 20 hours, the cell retention time was 30-50 hours, and the agitation rate was 800-900 rpm. The pH was 5.0 and the temperature was 38° C. Once the reactor reached steady state, the gas retention time was held constant at 11 minutes, the liquid retention time was set at 19 hours, the cell retention time was constant at 37 hours and the agitation rate was 900 rpm. The CO conversion averaged 96% and the $H_2$ conversion averaged 60%. The ethanol concentration steadied at 25-30 g/L, with about 3 g/L acetate also present. The ethanol productivity was 31.6-37.9 g/L·day.

EXAMPLE 17

Regulating the Fermentation Parameters to Avoid Acclimation to Low Limiting Calcium Pantothenate The acclimation of the culture in the fermentation bioreactor to low limiting calcium pantothenate concentration is avoided by regulating the fermentation parameters (gas rate, liquid rate, agitation rate, $H_2$ partial pressure) while avoiding major changes in nutrients, but instead maintaining a relatively constant nutrient feed concentration, as follows.

During start-up of a laboratory New Brunswick Scientific Bioflo® CSTR, *C. ljungdahlii*, strain C-01 was fed a liquid nutrient stream containing vitamins, trace minerals and salts necessary to provide nutrition to the culture. The pantothenate concentration in the nutrient medium was 20 µg/L, a concentration that when coupled with the slow rate of medium feed ensures that there is more than 100 µg calcium pantothenate fed per gram of cells produced (excess pantothenate) because of low cell production in the bioreactor. Similarly the cobalt concentration in the medium was 1 ppm, a concentration that ensures cobalt is also present in excess. Instead, the $H_2$ partial pressure in the exit gas was kept in excess of than 0.55 atmospheres by feeding a gas containing no $CO_2$, 63.3% $H_2$, 31.4% CO and 5.3% $C_2H_6$, thus yielding a ratio of $H_{2\,fed}/(2\,CO_{converted}$ and $3CO_{2\,converted})$ of more than 1 and by carefully regulating the gas feed rate and agitation rates to achieve greater than 95% CO conversion and greater than 80% $H_2$ conversion. As these high conversions are attained with time, the cell concentration builds from an initial level of near 0 g/L to about 1.5 g/L.

Since the pantothenate concentration is held constant during this start-up, the µg pantothenate per gram of cells produced gradually decreases until it is less than 15 µg pantothenate/g cell produced, a condition which is then pantothenate limited. The system thus grows into pantothenate limitation. High ethanol:acetate product ratios are attained throughout the start-up by excess $H_2$. Alternatively the reactor is allowed to produce acetic acid during the early stages of start-up, with the product ratio later brought under control through pantothenate limitation.

EXAMPLE 18

Limiting Cobalt to the Reactor

*C. ljungdahlii*, strain ERI-2 was fed 62 to 3500 µg cobalt/g cell produced during acetic acid production from CO, $CO_2$ and $H_2$, a condition where the reactor was not limited on cobalt (or any other limitation except for the ability to transfer gas to the culture), and no ethanol was found in the product stream. During limitation on cobalt for ethanol production from CO, $CO_2$ and $H_2$, *C. ljungdahlii* strain C-01 was fed 33 to 48 µg cobalt/g cells produced, while maintaining all other nutrients in excess. Under these conditions, strain C-01 produced 18 to 26 g/L ethanol and about 4 g/L acetate.

EXAMPLE 19

Avoiding Acclimation to Low Limiting Cobalt Concentration

Acclimation to low limiting cobalt concentration is avoided by regulating the fermentation parameters (gas rate, liquid rate, agitation rate, $CO_2$ content) while avoiding major changes in nutrients, but instead maintaining a relatively constant nutrient feed concentration, as follows.

During start-up of a laboratory New Brunswick Scientific Bioflo® CSTR, *C. ljungdahlii*, strain C-01 was fed a liquid nutrient stream containing vitamins, trace minerals and salts necessary to provide nutrition to the culture. The cobalt concentration in the nutrient medium was 75 ppb, a concentration that when coupled with the slow rate of medium feed ensures that there is more than 50 µg cobalt fed per g of cells produced (excess cobalt) because of low cell production in the bioreactor. Similarly the pantothenate concentration in the medium was 20 µg/L, a concentration that ensures pantothenate is also present in excess. Instead, the $H_2$ partial pressure in the exit gas was kept in excess of 0.55 atmospheres by feeding a gas containing large quantities of $H_2$ and no $CO_2$, and by carefully regulating the gas feed rate and agitation rates to achieve greater than 95% CO conversion and greater than 80% $H_2$ conversion. As these high conversions are attained with time, the cell concentration builds from an initial level of near 0 g/L to about 1.5 g/L. Since the cobalt concentration is held constant during this start-up, the µg cobalt per g cells produced gradually decreases until it is less than 50 µg cobalt/g cell produced, a condition which is then cobalt limited. The system thus grows into cobalt limitation. High ethanol yields are attained throughout the start-up by employing excess $H_2$ in the feed. Alternatively the reactor is allowed to produce acetic acid during the early stages of start-up, with the product ratio later brought under control through cobalt limitation.

EXAMPLE 20

Oversupplying Hydrogen

During operation of a laboratory AUTOKLAV™ reactor (Buchi) operated as a CSTR with liquid recirculation and cell recycle, *C. ljungdahlii* was operated with excess vitamins, trace minerals and salts necessary to provide nutrition to the culture. The reactor was operated with excess $H_2$ present in the feed gas such that the ratio of the moles of $H_2$ fed to the sum of two times the moles of CO converted and three times the moles of $CO_2$ converted was 5.67. If this ratio were not greater than 1.0, excess $H_2$ cannot be present in the reactor and ethanol production due to the presence of excess $H_2$ cannot occur. Furthermore, the $H_2$ partial pressure in the exit gas was 2.61 atm, a level that exceeds the requirement of 0.4 atm for ethanol production due to excess $H_2$. Finally, the ratio of $H_2$ partial pressure to $CO_2$ partial pressure in the exit gas was 10.88, a level which is greater than 3.0 and assures that enough $H_2$ is present to utilize all of the available carbon. Under these conditions the reactor produced nearly 26 g/L ethanol and less than 3 g/L acetate. The ethanol productivity was more than 200 g/L·day. If any of these above criteria are not met, the reactor cannot produce ethanol due to excess $H_2$ being present. Another aspect of $H_2$ abundance is that it results in additional reduced ferredoxin by oxidation through hydrogenase.

EXAMPLE 21

Alleviating CO Substrate Inhibition

A laboratory New Brunswick Scientific Bioflo® CSTR operating at an agitation rate of 800 rpm shows an outlet CO concentration of 10% when it had been previously operating with only 5% CO in the gas outlet. By decreasing the agitation rate to 600 rpm, CO inhibition was removed and the outlet CO concentration returned to 5%. This results in increased $H_2$ uptake, a necessary condition to efficiently utilize all of the gas fed to the reactor.

EXAMPLE 22

Mass Transfer

As an example of excess mass transfer leading to ethanol production, consider a laboratory CSTR with cell recycle containing *C. ljungdahlii*, strain ERI-2 operating without nutrient limitation or excess $H_2$ or CO in the feed gas. That is, pantothenate is fed at a rate of more than 100 µg calcium pantothenate per gram of cells produced and cobalt is fed at a rate of more than 100 µg per gram of cells produced. $H_2$ is present in the exit gas at about 0.2 atm and the specific CO uptake rate is less than 0.3 mmol CO/g cells·min. The agitation rate is 800 rpm. Under these conditions the culture produces only acetic acid (no ethanol present in the product stream). If the agitation rate is increased quickly to 900 rpm or the gas rate is increased by about 10%, ethanol is observed in the product stream, until the cell concentration increases in order to uptake the gas or until the culture dies due to substrate inhibition.

EXAMPLE 23

Controlling Acetic Acid Product Inhibition

In a laboratory CSTR which is producing 8 g/L acetic acid and 10 g/L ethanol, the liquid retention time is reduced from 24 hours to 12 hours for a period of 36 hours in an attempt to wash out the excess acetic acid from the reactor which is limiting the ability of the culture to produce more ethanol. All other reactor operating and nutrient conditions are held constant. After this period of time, the liquid retention time is returned to 24 hours and a product stream containing 3 g/L acetate and 15 to 25 g/L ethanol results. Several attempts in reducing the liquid retention time are required to clear the product inhibition. Alternatively, $H_2$ is added to the gas teed to allow excess $H_2$ control, since excess $CO_2$ can also lead to acetic acid production in favor of ethanol. These modifications prevent excess acetic acid production, and thus prevent a poor product ratio, and a low ethanol productivity. Thereafter, the use of excess $H_2$ in the feed gas or limiting liquid phase nutrient concentration is resumed.

EXAMPLE 24

Oversupplying Carbon Monoxide

*C. ljungdahlii*, strain ERI-2 when fed excess nutrients (pantothenate and cobalt in excess) and without an abundance of $H_2$ in the feed gas had a specific CO uptake rate of 0.23 to 0.48 mmol/g·min., and no ethanol was found in the product stream. However, when *C. ljungdahlii*, strain C-01 was similarly fed excess nutrients without an abundance of $H_2$, in the feed gas, but was under a condition where an oversupply of CO was causing ethanol production, the specific CO uptake rate was 0.67 to 1.34 mmol/g·min. Under these conditions the culture produced 9.9 to 12.0 g/L ethanol and 2.6 to 2.7 g/L acetate.

EXAMPLE 25

Controlling Product Ratios with Cell Purge

A gaseous substrate (30% CO, 15% $H_2$, 10% $CO_2$, 45% $N_2$) fermentation takes place in a CSTR (pH=5.0, Temperature=38° C., Pressure=20 psig) utilizing *C. ljungdahlii*, strain C-01, with cell recycle (cell retention time=40 hours and the liquid retention time=6 hours) and the culture is not limited in growth by cobalt, calcium pantothenate, or any other nutrient. As the culture grows, a cell density is attained such that the specific uptake (mmol CO per gram of dry cells per minute) is below 0.5 and acetic acid is produced preferentially to ethanol. To prevent this occurrence, the cell purge rate is increased to prevent an increase in cell density, such that the steady concentration of cells is kept low enough to maintain a specific uptake higher than 0.5 mmol CO per gram dry cells per minute. In doing so, the cell retention time is reduced to between 6 and 25 hours.

TABLE 1

Ethanol Production Medium

| Component | Quantity Per Liter |
|---|---|
| 2 g/l $FeCl_2 \cdot 4 H_2O$ | 10 mL |
| 85% $H_3PO_4$ | 0.05 mL |
| MPFN Trace Metals[a] | 20 mL |
| $(NH_4)_2HPO_4$ | 0.60 g |
| $NH_4Cl$ | 2.00 g |
| NaCl | 0.20 g |
| KCl | 0.15 g |
| $MgCl_2 \cdot 6H_2O$ | 0.50 g |
| $CaCl_2 \cdot 2H_2O$ | 0.20 g |
| Cysteine $HCl \cdot H_2O$ | 0.25 g |
| Vitamins solution[b] | variable[c] |

[a]MPFN Trace Metals contains (per liter of solution): 10 mL of 85% $H_3PO_4$, 0.10 g of $ZnSO_4 \cdot 7H_2O$, 0.03 g of $MnCl_2 \cdot 4H_2O$, 0.3 g of $H_3BO_3$, 0.20 g of $CoCl_2 \cdot 6H_2O$, 0.02 g of $CuCl_2 \cdot H_2O$, 0.04 g of $NiCl_2 \cdot 6H_2O$, 0.03 g of $NaMoO_4 \cdot 2H_2O$, 2.00 g of $FeCl_2 \cdot 4H_2O$, 0.01 g of $Na_2SeO_3$, and 0.10 g of $Na_2WO_4 \cdot 2H_2O$
[b]Vitamins solution contains 20.6 mg/L d-biotin, 50.6 mg/L thiamine HCl and 50.5 mg/L d-pantothenic acid, calcium salt
[c]Varies considerably from 0.3-0.5 mL at inoculation to as much as 0.7-0.8 mL at high gas rates

TABLE 2

Summary Comparison of Method Parameters and Results for Examples of Control Methods

| Example No. | Controlling Mechanism | Product Concentrations Ethanol (g/L) | Product Concentrations Acetate (g/L) | Ethanol Productivity (g/L · day) | Pantothenate Supplied (μg pantothenate/g cell produced) | Cobalt Supplied (μg Cobalt/g cell produced) | $\frac{H_{2\,Fed}}{(2CO_{conv} + 3CO_{2conv})}$ | $H_2$ Partial Pressure in Exit Gas (atm) | Specific CO Uptake (mmol/ g · cell · min) |
|---|---|---|---|---|---|---|---|---|---|
| 3 | Mass Transfer | 0 | 10-13 | 0 | 1575-3150 | 1734-3468 | 0.46 | 0.06-0.07 | 0.275-0.48 |
| 3 | Mass Transfer | 0 | 10-14 | 0 | 2250-3600 | 62-99 | 0.875 | 0.11-0.20 | 0.33-0.40 |
| 4 | Pantothenate | 15-19 | 1.5 | 11.5-14.5 | 18-24 | 5000-6660 | 1.03 | 0.55-0.64 | 0.23-0.30 |
| 4 | Pantothenate | 18 | 3 | 17.4 | 8.1 | 3960 | 1.14 | 0.60-0.65 | 0.33 |
| 5 | Cobalt | 26 | 4 | 15.6 | 15.2 | 33 | 0.94 | 0.63 | 0.37 |
| 5 | Cobalt | 18 | 4 | 27.0 | 85.7 | 47.6 | 1.03 | 0.60 | 0.50 |
| 6 | Excess CO | 9.9 | 2.6 | 29.0 | 97 | 83.6 | 1.09 | 1.6 | 1.34 |
| 6 | Excess CO | 12.0 | 2.7 | 60.0 | 294 | 735 | 0.30 | 0.6 | 0.67 |
| 7 | Excess $H_2$ | 10.0 | 3.3 | 6.7 | 900-1125 | 991-1239 | 1.96 | 0.7-0.87 | 0.28-0.35 |
| 7 | Excess $H_2$ | 25.96 | 2.85 | 215-240 | 46 | 460 | 5.67 | 2.61 | 1.68 |

TABLE 3

Summary of Product Shift with *Clostridium ljungdahlii* Strains

| C. ljungdahlii Strain | Medium Limitation | Cell Conc.* (g/L) | Gas Conversion (%) CO | Gas Conversion (%) H$_2$ | Product Concentration Ethanol | Product Concentration Acetate |
|---|---|---|---|---|---|---|
| ERI-2 | Acetic Acid Enhancing | 1.1 | 90 | 80 | 0 | 10 |
| ERI-2 | Pantothenate Limitation | 0.3 | 88 | 20 | 2.5 | 0 |
| ERI-2 | Acetic Acid Enhancing | 0.55 | 90 | 85 | 1.0 | 5.5 |
| ERI-2 | Pantothenate Limitation | 0.5 | 90 | 20 | 10 | 1.0 |
| ERI-2 | Acetic Acid Enhancing | 0.8 | 100 | 93 | 1 | 7 |
| ERI-2 | Cobalt Limitation | 1.3 | 80 | 20 | 9 | 3 |
| C-01 | Acetic Acid Enhancing | 1.2 | 96 | 90 | 1 | 8 |
| C-01 | Pantothenate Limitation | 0.8 | 60 | 30 | 4 | 0 |
| C-01 | Acetic Acid Enhancing | 1.2 | 96 | 90 | <1 | 9 |
| C-01 | Cobalt Limitation | 2.5 | 80 | 20 | 17 | 2 |
| PETC | Acetic Acid Enhancing | 0.8 | 65 | 55 | 2 | 10 |
| PETC | Cobalt Limitation | 1.0 | 95 | 55 | 8 | 1 |

*Dry cell weight basis

TABLE 4

Steady State Data for the Conversion of CO-Rich Gas to Ethanol Using *C. ljungdahlii*, Strain C-01

| GRT (min) | LRT (hr) | Agitation Rate (rpm) | Cell Conc* (g/L) | Gas Conversion (%) CO | Gas Conversion (%) H$_2$ | Products (g/L) Ethanol | Products (g/L) Acetate | Ethanol Productivity (g/L · day) |
|---|---|---|---|---|---|---|---|---|
| 13 | 32.4 | 700 | 2.44 | 91 | 57 | 21.6 | 3.9 | 16.0 |
| 11.93 | 25.7 | 750 | 2.51 | 92 | 54 | 20.6 | 3.6 | 19.2 |
| 12.67 | 25.6 | 750 | 2.60 | 93 | 61 | 18.7 | 4.7 | 17.6 |
| 10 | 24.5 | 750 | 2.75 | 92 | 43 | 20.4 | 6.1 | 20.0 |
| 11.54 | 23.8 | 750 | 2.65 | 92 | 40 | 20.4 | 5.3 | 20.6 |
| 12.10 | 23.8 | 750 | 2.77 | 88 | 18 | 21 | 3.1 | 21.1 |
| 13.8 | 23.8 | 750 | 2.70 | 90 | 25 | 18 | 2.5 | 18.2 |
| 12.7 | 23.8 | 750 | 2.70 | 92 | 35 | 20 | 3.8 | 20.2 |
| 13.3 | 24.0 | 800 | 2.70 | 85 | 10 | 17.5 | 5.0 | 17.5 |
| 14.81 | 31 | 750 | 2.50 | 92 | 30 | 25 | 2.5 | 19.4 |
| 16.9 | 31 | 750 | 3.60 | 90 | 18 | 23 | 3.0 | 17.8 |
| 18.5 | 33 | 750 | 2.60 | 94 | 50 | 24 | 3.5 | 17.5 |
| 17.2 | 34 | 750 | 2.50 | 91 | 40 | 24 | 3.5 | 16.9 |
| 18.5 | 34 | 750 | 2.30 | 95 | 63 | 23 | 4.0 | 16.2 |
| 19.2 | 40.6 | 750 | 2.70 | 94 | 50 | 28.5 | 4.0 | 17.4 |
| 19.0 | 55 | 750 | 2.70 | 94 | 20 | 33 | 4.0 | 14.4 |

*Dry cell weight basis

TABLE 5

Steady State Data for the Conversion of Gas Containing 27% CO, 16% H$_2$, 51% N$_2$ to Ethanol Using *C. ljungdahlii*, Strain C-01. No Cell Recycle

| GRT (min) | LRT (hr) | Agitation Rate (rpm) | Cell Conc* (g/L) | Gas Conversion (%) CO | Gas Conversion (%) H$_2$ | Products (g/L) Ethanol | Products (g/L) Acetate | Ethanol Productivity (g/L · day) |
|---|---|---|---|---|---|---|---|---|
| 8.89 | 23.8 | 750 | 2.3 | 84 | 57 | 11 | 2.5 | 11.1 |
| 8.3 | 23.8 | 900 | 2.6 | 89 | 55 | 12 | 2.0 | 12.1 |
| 8.3 | 27.7 | 900 | 2.7 | 89 | 47 | 15 | 3.0 | 13.0 |
| 7.1 | 33.3 | 900 | 3.0 | 86 | 37 | 19 | 3.0 | 13.7 |
| 7.4 | 33.3 | 900 | 3.0 | 87 | 40 | 19.5 | 3.0 | 14.1 |
| 6.34 | 33.3 | 900 | 3.0 | 86 | 37 | 21 | 3.5 | 15.1 |
| 6.18 | 33.3 | 900 | 3.0 | 86 | 41 | 20.9 | 3.1 | 15.1 |
| 5.72 | 34.3 | 900 | 3.0 | 85 | 40 | 22.1 | 3.8 | 15.5 |
| 5.12 | 33 | 900 | 3.7 | 85 | 40 | 25.0 | 4.0 | 18.2 |
| 4.59 | 33 | 900 | 4.1 | 83 | 33 | 25 | 3.5 | 18.2 |
| 4.59 | 29 | 900 | 4.0 | 80 | 35 | 23 | 4.0 | 19.0 |
| 4.76 | 29 | 900 | 3.9 | 90 | 35 | 19 | 5.0 | 15.7 |
| 4.25 | 28 | 900 | 4.2 | 80 | 30 | 23 | 3.0 | 19.7 |
| 5.5 | 37 | 900 | 3.4 | 84 | 40 | 23 | 3.0 | 14.9 |
| 5.26 | 31 | 900 | 3.8 | 84 | 50 | 23 | 3.0 | 17.8 |
| 5.71 | 31 | 900 | 3.7 | 80 | 28 | 26 | 3.5 | 20.1 |
| 6.25 | 31 | 900 | 3.75 | 82 | 30 | 25.5 | 3.0 | 19.7 |
| 6.66 | 31 | 900 | 3.6 | 86 | 64 | 22 | 4.0 | 17.0 |

TABLE 6

Steady State Data for the Conversion of Gas Containing 50% H$_2$, 45% CO and 5% CH$_4$ to Ethanol Using Isolate O-52 in a CSTR with Cell Recycle

| GRT (min) | XRT (hr) | LRT (hr) | Cell Conc* (g/L) | Gas Conversion (%) CO | Gas Conversion (%) H$_2$ | Products (g/L) Ethanol | Products (g/L) Acetate | Ethanol Productivity (g/L · day) |
|---|---|---|---|---|---|---|---|---|
| 12.5 | 46.4 | 23.2 | 3.8 | 96.3 | 81.2 | 20.4 | 4.4 | 21.1 |
| 9.7 | 43.2 | 17.3 | 4.9 | 86.7 | 49.9 | 21.1 | 3.5 | 29.3 |
| 9.2 | 43.2 | 17.3 | 4.6 | 89.4 | 64.5 | 20.5 | 5.1 | 28.4 |
| 7.5 | 43.2 | 17.3 | 5.0 | 81.8 | 42.1 | 22.2 | 3.7 | 30.8 |
| 9.2 | 49.4 | 17.3 | 4.6 | 85.3 | 52.1 | 21.1 | 4.4 | 29.3 |
| 8.4 | 46.0 | 16.1 | 4.5 | 85.2 | 61.4 | 20.8 | 5.1 | 31.0 |
| 6.8 | 54.3 | 16.3 | 4.7 | 84.7 | 57.7 | 23.4 | 5.7 | 34.5 |
| 7.2 | 54.3 | 16.3 | 4.0 | 83.1 | 55.2 | 19.0 | 4.4 | 28.0 |
| 7.4 | 54.3 | 16.3 | 5.0 | 86.3 | 66.7 | 21.9 | 5.5 | 32.2 |
| 6.4 | 55.6 | 16.7 | 5.6 | 83.3 | 53.1 | 23.5 | 4.9 | 33.8 |
| 6.2 | 41.6 | 14.5 | 5.7 | 82.5 | 55.0 | 20.1 | 5.0 | 33.3 |
| 6.0 | 41.6 | 14.5 | 6.0 | 82.5 | 50.0 | 21.5 | 3.0 | 35.6 |
| 6.0 | 34.2 | 12.0 | 5.7 | 84.0 | 56.0 | 19.5 | 4.5 | 39.0 |
| 5.7 | 34.2 | 12.0 | 5.7 | 81.0 | 45.0 | 18.0 | 4.5 | 36.0 |

*Dry cell weight basis

TABLE 7 pH and Liquid Sample Analyses in Shifting Acetate to Ethanol in the Presence of Excess CO

| Time | pH | Cell Conc.* (g/L) | Ethanol (g/L) | Acetate (g/L) | Butanol (g/L) |
|---|---|---|---|---|---|
| 0 | 4.69 | 2.4 | 10.3 | 3.1 | 0.3 |
| 30 | 5.28 | | 11.4 | 1.5 | 0.3 |
| 35 | 5.28 | 2.4 | 11.6 | 1.6 | 0.3 |

TABLE 7-continued pH and Liquid Sample Analyses in Shifting Acetate to Ethanol in the Presence of Excess CO

| Time | pH | Cell Conc.* (g/L) | Ethanol (g/L) | Acetate (g/L) | Butanol (g/L) |
|---|---|---|---|---|---|
| 50 | 4.98 | | 11.3 | 1.8 | 0.3 |
| 80 | 4.73 | 2.4 | 10.9 | 2.9 | 0.3 |

*Based on dry cell weight

TABLE 8

Data for Gas Fermentation by Isolate O-52 with Cell and Water Recycle

| Time (hr) | % Water Recycle | Cell Conc.* (g/L) | Gas Conversion CO (%) | Gas Conversion $H_2$ (%) | Ethanol (g/L) | Acetate (g/L) | Net Acetate (g/L) | Ethanol Productivity (g/L · day) |
|---|---|---|---|---|---|---|---|---|
| 0-75 | 25 | 2.1 | 95 | 68 | 12 | 4 | 4 | 12 |
| 75-193 | 50 | 2.1 | 95 | 75 | 15 | 6 | 5 | 15 |
| 193-462 | 75 | 2.1 | 92 | 60 | 17 | 5 | 4 | 17 |
| 462-554 | 50 | 1.6 | 85 | 30 | 17→13 | 5 | 3 | 12-16 |
| 554-669 | 75 | 2.6 | 92 | 75 | 13→19 | 5 | 3 | 12-18 |
| 669-943 | 100 | 3.0 | 92 | 70 | 23 | 6 | 3 | 23 |
| 943-1087 | 100 | 3.0 | 92 | 60 | 23 | 6 | 0 | 23 |
| 1087-1232 | 100 | 2.7 | 92 | 60 | 23 | 6 | −0 | 23 |
| 1232-1375 | 100 | 3.0 | 91 | 60 | 27 | 6 | −1 | 27 |
| 1375-1534 | 100 | 3.5 | 88 | 35 | 23 | 5 | 0 | 23 |

*Dry cell weight basis

All published documents are incorporated by reference herein. Numerous modifications and variations of the present invention are included in the above-identified specification and are expected to be obvious to one of skill in the art. Such modifications and alterations to the compositions and methods of the present invention are believed to be encompassed in the scope of the claims appended hereto.

We claim:

1. A continuous method for producing ethanol comprising: culturing in a fermentation bioreactor at least one strain of *Clostridium ljungdahlii* bacteria in a continuously fed liquid nutrient medium to provide a fermentation broth; supplying to said fermentation bioreactor a gaseous substrate comprising carbon monoxide; and maintaining a specific rate of CO uptake in said fermentation bioreactor at an amount of 0.3 to 2 mmol CO/gram dry cells weight of bacteria per minute in the fermentation broth after the bacteria achieve a stable cell concentration in the fermentation bioreactor; wherein the bacteria produce both ethanol and acetate in a ratio of ethanol to acetate ranging from 1:1 to 20:1; wherein $(H_{2\ Fed})/(2CO_{conv}+3CO_{2\ conv})$ ranges from 0.46 to 5.67; and wherein the pH is greater than 4.5.

2. The method of claim 1, wherein at least one strain of *Clostridium ljungdahlii* bacteria is *Clostridium ljungdahlii* PETC, *Clostridium ljungdahlii* ER12, *Clostridium ljungdahlii* C-01, *Clostridium ljungdahlii* O-52, or mixed strains.

3. The method of claim 1, wherein said gaseous substrate is selected from the group consisting of (a) carbon monoxide, (b) carbon monoxide and hydrogen, and (c) carbon monoxide, carbon dioxide and hydrogen.

4. The method of claim 1, wherein the gaseous substrate comprises carbon monoxide and hydrogen in a ratio of carbon monoxide to hydrogen ranging from 0.25 to 3.25.

5. The method of claim 1, wherein the gaseous substrate additionally comprises at least one gas chosen from nitrogen and methane.

6. The method of claim 1 further comprising supplying calcium pantothenate in an amount ranging from 2 to 50 µg calcium pantothenate per gram of dry cells of bacteria in the fermentation bioreactor.

7. The method of claim 1 further comprising supplying cobalt in an amount ranging from 5 to 100 µg cobalt per gram of dry cells of bacteria in the fermentation bioreactor.

8. The method of claim 1 further comprising supplying cobalt, wherein the cobalt is maintained at a constant concentration.

9. The method of claim 1, wherein the fermentation bioreactor consists of one or more: continuous stirred tank reactor (CSTR), immobilized cell reactor (ICR), trickle bed reactor (TBR), bubble column, gas lift fermenter, and static mixer.

10. The method of claim 1, wherein the fermentation bioreactor comprises a growth reactor that feeds the fermentation broth to a second fermentation bioreactor in which some or all of the ethanol is produced.

11. The method of claim 1 further comprising: removing the fermentation broth from the fermentation bioreactor; distilling ethanol from the broth; and recovering the ethanol.

12. The method of claim 1 further comprising purging the bacteria from the fermentation bioreactor.

13. The method of claim 1, wherein the pH ranges from 4.5 to 5.5.

* * * * *

UNITED STATES PATENT AND TRADEMARK OFFICE
CERTIFICATE OF CORRECTION

PATENT NO. : 8,574,879 B2  
APPLICATION NO. : 13/325149  
DATED : November 5, 2013  
INVENTOR(S) : James L Gaddy et al.

Page 1 of 1

It is certified that error appears in the above-identified patent and that said Letters Patent is hereby corrected as shown below:

In the Specification:

Col. 1, line 17 insert-
--This invention was made with government support under Grant Nos. DE-FC04-94AL98770, 85X-TA046V, and 85X-SX613V, awarded by the US Department of Energy, and under Grant No. 96-AARC-1-0077, awarded by the US Department of Agriculture. The government has certain rights in the invention.--

Signed and Sealed this
Thirteenth Day of May, 2014

Michelle K. Lee
*Deputy Director of the United States Patent and Trademark Office*